United States Patent
Davey et al.

(10) Patent No.: US 6,525,051 B2
(45) Date of Patent: Feb. 25, 2003

(54) N-HETEROCYCLIC DERIVATIVES AS NOS INHIBITORS

(75) Inventors: David D. Davey, El Sobrante, CA (US); Eric Pham, Berkeley, CA (US); Gary B. Phillips, Pleasant Hill, CA (US); Wei Xu, Danville, CA (US)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/814,787

(22) Filed: Mar. 22, 2001

(65) Prior Publication Data

US 2002/0010190 A1 Jan. 24, 2002

Related U.S. Application Data

(60) Provisional application No. 60/192,168, filed on Mar. 27, 2000.

(51) Int. Cl.[7] .................... C07D 405/14; A61K 31/44; A61K 31/506
(52) U.S. Cl. .................... 514/235.8; 514/252.19; 514/269; 514/274; 514/341; 544/123; 544/310; 544/319; 546/272.7
(58) Field of Search ................ 544/123, 310, 544/319; 546/272.7; 514/235.8, 252.19, 269, 274, 341

(56) References Cited

U.S. PATENT DOCUMENTS

| | | | |
|---|---|---|---|
| 5,244,865 A | 9/1993 | Seltz et al. | 504/239 |
| 5,426,110 A | 6/1995 | Gossett et al. | 514/275 |
| 5,489,591 A | 2/1996 | Kobayashi et al. | 514/245 |
| 5,663,334 A | 9/1997 | Sheldrake et al. | 544/122 |

FOREIGN PATENT DOCUMENTS

| | | |
|---|---|---|
| EP | 0 257 850 A2 | 3/1988 |
| EP | 0 640 599 A1 | 3/1995 |
| WO | WO96/14842 | 5/1996 |
| WO | WO96/14844 | 5/1996 |
| WO | WO98/09960 | 3/1998 |
| WO | WO98/37079 | 8/1998 |

OTHER PUBLICATIONS

Molina et al., PubMed Abstract (Drugs Aging 12(4): 251–9), 1998.*
Grunblatt et al., PubMed Abstract (Ann N Y Acad. Sci, 899:262–73), 2000.*
Le Corvoisier et al., PubMed Abstract (J. Soc. Biol. 194(3–4): 143–9), 2000.*
Feihl et al., PubMed Abstract (Pharmacol. Ther. 91(3):179–213), 2001.*
Perner et al., PubMed Abstract (Aliment Pharmacol. Ther. 13(2): 135–44), 1999.*
Bogdan, PubMed Abstract (Nat. Immunol., 2(10): 907–16), 2001.*
Damasio, Alzheimer's Disease And Related Dementias, Cecil Textbook of Medicine, 20th Edition, vol. 2, pp. 1992–1996, 1996.*
Simone, Oncology: Introduction, Cecil Textbook of Medicine, 20th Edition, vol. 1, pp. 1004–1010, 1996.*

(List continued on next page.)

Primary Examiner—Deepak Rao
(74) Attorney, Agent, or Firm—Carol J. Roth

(57) ABSTRACT

N-Heterocyclic derivatives selected from the group consisting of the following formulae:

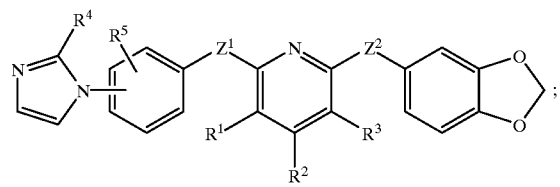

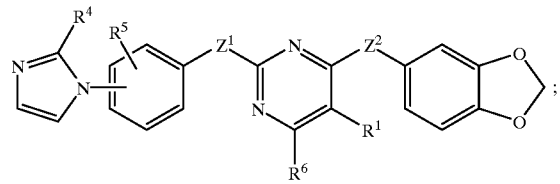

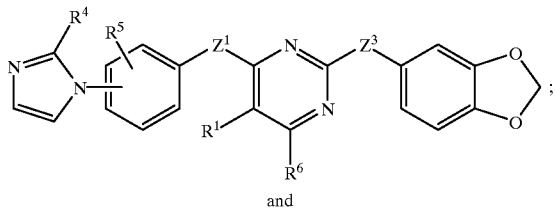

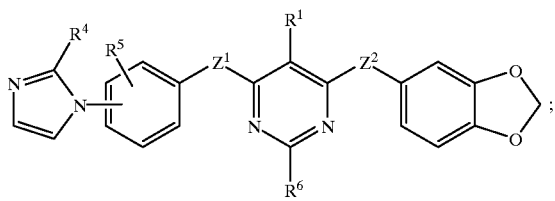

where $Z^1$, $Z^2$, $Z^3$, $R^1$, $R^2$, $R^3$, $R^4$, $R^5$ and $R^6$ are described herein, are useful as inhibitors of nitric oxide synthase. Pharmaceutical compositions containing these compounds, methods of using these compounds as inhibitors of nitric oxide synthase and processes for synthesizing these compounds are also described herein.

36 Claims, No Drawings

OTHER PUBLICATIONS

Feldman et al., "The Surprising Life of Nitric Oxide", *Chemical and Engineering News* (1993) 26–38.

Del Corona et al., "Synthesis and in vitro study of platelet antiaggregant activity of 2(4)–imidazol–1–yl–4(2)–cycloalkylaminopyrimidines", *Eur. J. Med. Chem.* (1991) 26(7):729–733.

Fujisawa et al., "Inducible Nitric Oxide Synthase in a Human Glioblastoma Cell Line", *J. Neurochem.*(1995) 64(1):85–91.

Nathan, "Nitric oxide as a secretory product of mammalian cells", *FASEB Journal* (1992) 6:3052:3064.

Lampe et al., "A Novel Rearrangement of 1–(2–Aminoaryl)-imidazoles", *J. Heterocyclic Chem* (1994) 31:287–291.

* cited by examiner

N-HETEROCYCLIC DERIVATIVES AS NOS INHIBITORS

This application claims the benefit of U.S. Provisional Application No. 60/192,168, filed Mar. 27, 2000, which is incorporated herein in full by reference.

FIELD OF THE INVENTION

The invention relates to a series of N-heterocyclic compounds and derivatives useful as inhibitors of nitric oxide synthase (NOS) and to methods of therapy for various diseases employing those compounds.

BACKGROUND OF THE INVENTION

Nitric oxide (NO) has been implicated in a number of diverse physiological processes, including smooth muscle relaxation, platelet inhibition, nerve transmission, immune regulation and penile erection. Nitric oxide is produced under various conditions by virtually all nucleated mammalian cells. A number of pathologies are ascribed to abnormalities in NO production including stroke, insulin dependent diabetes, septic shock-induced hypotension, rheumatoid arthritis and multiple sclerosis. Nitric oxide is synthesized in biological tissues by an enzyme called nitric oxide synthase (NOS) which uses NADPH and molecular oxygen to oxidize L-arginine to citrulline and NO.

Nitric oxide synthase exists in at least three isoforms, which fall into two primary categories: constitutive and inducible. Two constitutive isoforms, which are calcium and calmodulin dependent, have been identified, and one inducible isoform has been identified. The constitutive isoforms are (1) a neuronal isoform, NOS-1 or nNOS, which is found in the brain and skeletal muscles and (2) an endothelial isoform, NOS-3 or eNOS, which is expressed in the endothelium of blood vessels, the epithelium of the bronchial tree and in the brain. These constitutive isoforms are not the target of the NOS inhibitors of the present invention.

The inducible isoform (NOS-2 or iNOS) is expressed in virtually all nucleated mammalian cells following exposure to inflammatory cytokines or lipopolysaccharide. Its presence in macrophages and lung epithelial cells is particularly noteworthy. The inducible isoform is neither stimulated by calcium nor blocked by calmodulin antagonists. It contains several tightly bound co-factors, including FMN, FAD and tetrahydrobiopterin.

Nitric oxide generated by the inducible form of NOS has been implicated in the pathogenesis of inflammatory diseases. In experimental animals, hypotension induced by lipopolysaccharide or tumor necrosis factor a can be reversed by NOS inhibitors. Conditions which lead to cytokine-induced hypotension include septic shock, hemodialysis and interleukin therapy in cancer patients. It is expected that an INOS inhibitor would be effective in treating cytokine-induced hypotension. In addition, recent studies have suggested a role for NO in the pathogenesis of inflammation, and NOS inhibitors would therefore have beneficial effects on inflammatory bowel disease, cerebral ischemia and arthritis. Inhibitors of NOS may also be useful in treating adult respiratory distress syndrome (ARDS) and myocarditis, and they may be useful as adjuvants to short term immunosuppression in transplant therapy.

The diversity and ubiquity of NO function in physiology make the specific therapeutic targeting of NO-related phenomena an important consideration. Since endogenous NO production is the result of the actions of related but distinct isozymes, the differential inhibition of NOS isozymes allows more selective therapy with fewer side effects.

SUMMARY OF THE INVENTION

The compounds of the invention are inhibitors of iNOS and are therefore useful in conditions associated with the excessive production of NO. Accordingly, in one aspect, the invention is directed to compounds selected from the group consisting of the following formulae:

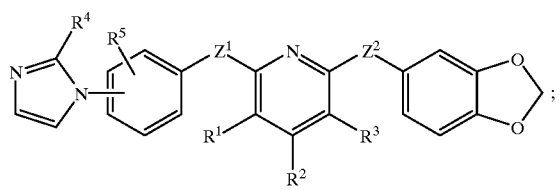

(I)

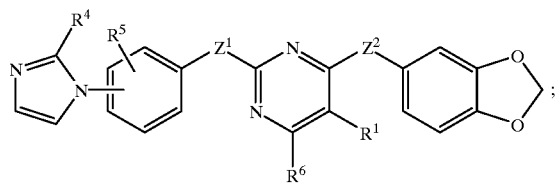

(II)

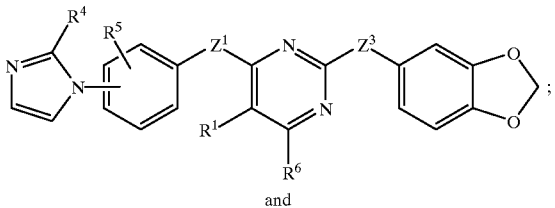

(III)

and

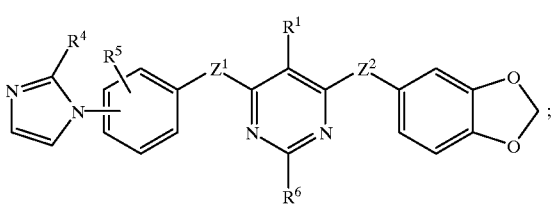

(IV)

wherein:

each $Z^1$ is independently —$(CH_2)_m$—O— (where m is 0 to 2), —$(CH_2)_m$—S— (where m is 0 to 2), or —$(CH_2)_m$—N($R^7$)— (where m is 0 to 2);

each $Z^2$ is independently —O—$(CH_2)_m$— (where m is 0 to 2), —S—$(CH_2)_m$— (where m is 0 to 2), or —N($R^7$)—$(CH_2)_m$— (where m is 0 to 2);

$Z^3$ is —$(CH_2)_n$— (where n is 1 to 4), —O—$(CH_2)_m$— (where m is 0 to 2), —S—$(CH_2)_m$— (where m is 0 to 2), or —N($R^7$)—$(CH_2)_m$— (where m is 0 to 2);

each $R^1$ and $R^3$ are independently selected from the group consisting of hydrogen, halo, alkyl, haloalkyl, nitro, aralkoxy, —$OR^8$, —$R^{11}$—$OR^8$, —$N(R^8)R^9$, —C(O)$OR^8$, —$R^{11}$—C(O)$OR^8$, —C(O)N($R^8$)$R^9$, —$R^{11}$—C(O)N($R^8$)$R^9$, —C(O)N($R^8$)$CH_2$C(O)N($R^8$)$R^9$, —N($R^8$)C(O)N($R^8$)$R^9$, —N($R^8$)C(O)$R^9$, —N($R^8$)S(O)$_2R^{10}$, and —N($R^8$)C(O)N($R^8$)—$CH_2$C(O)N($R^8$)$R^9$;

$R^2$ is hydrogen, alkyl, bromo, iodo, —N($R^7$)—$(CH_2)_p$—N($R^8$)$R^9$ (where p is 1 to 4), —$(CH_2)_q$—N($R^7$)—

$CH_2$—C(O)—$OR^8$ (where q is 0 to 3), 4-morpholinyl, 1-piperidinyl, 1-piperazinyl, or 1-pyrrolidinyl;

each $R^4$ is independently hydrogen or alkyl;

each $R^5$ is independently hydrogen, halo, haloalkyl, alkyl, nitro, —$OR^8$, —C(O)$OR^8$, —C(O)N($R^8$)$R^9$, —N($R^8$)$R^9$, —N($R^8$)C(O)$R^8$, or —N(H)S(O)$_2R^{10}$;

each $R^6$ is independently hydrogen, alkyl, aryl, aralkyl, halo, —N($R^8$)$R^9$, —N($R^7$)—(CH$_2$)$_p$—N($R^8$)$R^9$ (where p is 1 to 4), —(CH$_2$)$_q$—N($R^7$)—CH$_2$—C(O)$OR^8$ (where q is 0 to 3), 4-morpholinyl, 1-piperidinyl, 1-piperazinyl, or 1-pyrrolidinyl;

each $R^7$ is hydrogen or alkyl;

each $R^8$ and $R^9$ is independently hydrogen, alkyl, aryl (optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), or aralkyl (wherein the aryl is optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl);

each $R^{10}$ is alkyl, aryl (optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), or aralkyl (wherein the aryl is optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), and each $R^{11}$ is independently an alkylene or alkylidene chain;

as a single stereoisomer or a mixture thereof; or a pharmaceutically acceptable salt thereof.

In another aspect, the invention is directed to pharmaceutical compositions useful in treating a condition in a mammal resulting from an abnormality in NO production, which compositions comprise a compound of the invention as described above and a pharmaceutically acceptable excipient.

In another aspect, the invention is directed to methods of treating a condition resulting from an abnormality in NO production which methods comprise administering to a mammal having a condition resulting from an abnormality in NO production a therapeutically effective amount of a compound of the invention as described above.

DETAILED DESCRIPTION OF THE INVENTION

A. Definitions

As used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to six carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like.

"Alkoxy" refers to a radical of the formula —$OR_a$ where $R_a$ is an alkyl radical as defined above, e.g., methoxy, ethoxy, n-propoxy, 1-methylethoxy (iso-propoxy), n-butoxy, n-pentoxy, 1,1-dimethylethoxy (t-butoxy), and the like.

"Alkoxycarbonyl" refers to a radical of the formula —C(O)$OR_a$ where $R_a$ is an alkyl radical as defined above, e.g., methoxycarbonyl, ethoxycarbonyl, n-propoxycarbonyl, 1-methylethoxycarbonyl(iso-propoxycarbonyl), n-butoxycarbonyl, n-pentoxycarbonyl, 1,1-dimethylethoxycarbonyl(t-butoxycarbonyl), and the like.

"Amino" refers to the radical —$NH_2$.

"Aryl" refers to a phenyl or naphthyl radical.

"Aralkyl" refers to a radical of the formula —$R_aR_b$ where $R_a$ is an alkyl radical as defined above, substituted by $R_b$, an aryl radical, as defined above, e.g., benzyl.

"Arylcarbonyl" refers to a radical of the formula —C(O)—$R_b$ where $R_b$ is an aryl radical as defined above, e.g., phenylcarbonyl.

"Aralkoxy" refers to a radical of the formula —$OR_c$ where $R_c$ is an aralkyl radical as defined above, e.g., benzyloxy, and the like.

"Aminocarbonyl" refers to the radical —C(O)$NH_2$.

"Carboxy" refers to the radical —C(O)OH.

"Dialkylamino" refers to a radical of the formula —N($R_a$)$R_a$ where each $R_a$ is independently an alkyl radical as defined above, e.g., dimethylamino, methylethylamino, diethylamino, dipropylamino, ethylpropylamino, and the like.

"Dialkylaminocarbonyl" refers to a radical of the formula —C(O)N($R_a$)$R_a$ where each $R_a$ is independently an alkyl radical as defined above, e.g., dimethylaminocarbonyl, methylethylaminocarbonyl, diethylaminocarbonyl, dipropylaminocarbonyl, ethylpropylaminocarbonyl, and the like.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Mammal" includes humans and domesticated animals, including, without limitation, mice, rats, cattle, horses, swine, sheep, goats, dogs, cats, rabbits, and the like.

"Monoalkylamino" refers to a radical of the formula —$NHR_a$ where $R_a$ is an alkyl radical as defined above, e.g., methylamino, ethylamino, propylamino, and the like.

"Monoalkylaminocarbonyl" refers to a radical of the formula —C(O)$NHR_a$ where $R_a$ is an alkyl radical as defined above, e.g., methylaminocarbonyl, ethylaminocarbonyl, propylaminocarbonyl, and the like.

"Nitro" refers to —$NO_2$.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Particularly preferred organic bases are isopropylamine, diethylamine, ethanolamine, trimethylamine, dicyclohexylamine, choline and caffeine.

"Therapeutically effective amount" refers to that amount of a compound of the invention which, when administered to a mammal, preferably a human, in need thereof, is sufficient to effect treatment, as defined below, for a condition resulting from an abnormality in NO production. The amount of a compound of the invention which constitutes a "therapeutically effective amount" will vary depending on the compound, the condition and its severity, and the age of the mammal, preferably a human, to be treated, but can be determined routinely by one of ordinary skill in the art having regard to his own knowledge and to this disclosure.

"Treating" or "treatment" as used herein covers the treatment of a condition in a mammal, preferably a human, which condition is characterized by an abnormality in NO production, and includes:
(i) preventing the condition from occurring in the mammal, in particular, when such mammal is predisposed to the condition but has not yet been diagnosed as having it;
(ii) inhibiting the condition, i.e., arresting its development; or
(iii) relieving the condition, i.e., causing regression of the condition.

The yield of each of the reactions described herein is expressed as a percentage of the theoretical yield.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (R)- and (S)-, or (D)- and (L)- isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The nomenclature used herein is a modified form of the I.U.P.A.C. nomenclature system wherein the compounds of the invention are named herein as derivatives of the central N-heterocyclic moiety. For example, the following compound of the invention:

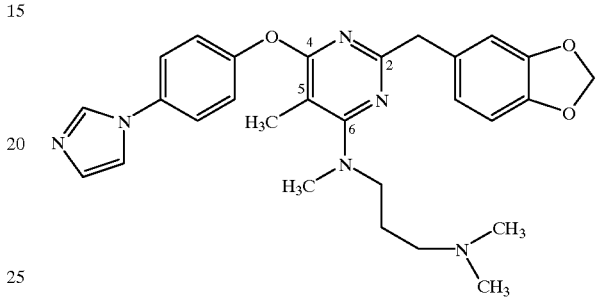

is named herein as 2-[(1,3-benzodioxol-5-yl)methyl]-6-[3-(dimethylamino)propyl(methyl)amino]-4-[4-(1H-imidazol-1-yl)phenoxy]-5-methylpyrimidine. Unless otherwise indicated, compound names are intended to include any single stereoisomer, enantiomer, racemate or mixtures thereof.

B. Utility of the Compounds of the Invention

Nitric oxide generated by the inducible form of nitric oxide synthase (iNOS) has been implicated in the pathogenesis of numerous inflammatory and autoimmune diseases and also in diseases which are generally not regarded as inflammatory, but nevertheless may involve cytokines which locally up-regulate iNOS. The compounds of the invention, alone or in combination with other pharmaceutical agents, are therefore useful in treating mammals, preferably humans, having a condition resulting from an abnormality in NO production. Such conditions include, but are not limited to, the following:

Multiple sclerosis (Parkinson, J. F. et al., *J. Mol. Med.* (1997), Vol. 75, pp. 174–186); stroke or cerebral ischemia (Iadecola, C. et al., *J. Neurosci.* (1997), Vol. 17, pp. 9157–9164); Alzheimer's disease (Smith, M. A. et al., *J. Neurosci.* (1997), Vol. 17, pp. 2653–2657; Wallace, M. N. et al., *Exp. Neurol.* (1997), Vol. 144, pp. 266–272); HIV dementia (Adamson, D. C. et al., *Science* (1996), Vol. 274, pp. 1917–1921); Parkinson's disease (Hunot, S. et al, *Neuroscience* (1996), Vol. 72, pp. 355–363); meningitis (Koedel, U. et al., *Ann. Neurol.* (1995), Vol. 37, pp. 313–323); dilated cardiomyopathy and congestive heart failure (Satoh M et al., *J. Am. Coll. Cardiol.* (1997), Vol. 29, pp. 716–724); atherosclerosis (Wilcox, J. N. et al., *Arterioscler. Thromb. Vasc. Biol.* (1997), Vol. 17, pp. 2479–2488); restenosis or graft stenosis, septic shock and hypotension (Petros, A. et al., *Cardiovasc. Res.* (1994), Vol. 28, pp. 34–39); hemorrhagic shock (Thiemermann, C. et al., *Proc. Natl. Acad. Sci.* (1993), Vol. 90, pp. 267–271); asthma (Barnes, P. J., *Ann. Med.* (1995), Vol. 27, pp. 389–393; Flak, T. A. et al., *Am. J. Respir. Crit. Care Med.* (1996), Vol. 154, pp. S202–S206); adult respiratory distress syndrome, smoke or particulate-mediated lung injury (Ischiropoulos, H. et al., Am. J. Respir. Crit. Care Med. (1994), Vol. 150, pp. 337–341; Van Dyke, K., Agents Actions (1994), Vol. 41, pp. 44–49); pathogen-mediated pneumonias (Adler, H. et al., J. Exp. Med. (1997), Vol. 185, pp. 1533–1540); trauma of various etiologies (Thomae, K. R. et al., Surgery (1996), Vol. 119, pp. 61–66); rheumatoid arthritis and osteoarthritis (Grabowski, P. S. et al., Br. J. Rheumatol. (1997), Vol. 36, pp. 651–655); glomerulonephritis (Weinberg, J. B. et al., J. Exp. Med. (1994), Vol. 179, pp. 651–660); systemic lupus erythematosus (Belmont, H. M. et al., Arthritis Rheum. (1997), Vol. 40, pp. 1810–1816); inflammatory bowel diseases such as ulcerative colitis and Crohn's disease (Godkin, A. J. et al., Eur. J. Clin. Invest. (1996), Vol. 26, pp. 867–872; Singer, I. I. et al., Gastroenterology (1996), Vol. 111, pp. 871–885); insulin dependent diabetes mellitus (McDaniel, M. L., et al., Proc. Soc. Exp. Biol. Med. (1996), Vol. 211, pp. 24–32); diabetic neuropathy or nephropathy (Sugimoto, K. and Yagihashi, S., Microvasc. Res. (1997), Vol. 53, pp. 105–112; Amore, A. et al., Kidney Int. (1997), Vol. 51, pp. 27–35); acute and chronic organ transplant rejection (Worrall, N. K. et al., Transplantation (1997), Vol. 63, pp. 1095–1101); transplant vasculopathies (Russell, M. E. et al., (1995), Vol. 92, pp. 457–464); graft-versus-host disease (Kichian, K. et al., J. Immunol. (1996), Vol. 157, pp. 2851–2856); psoriasis and other inflammatory skin diseases (Bruch-Gerharz, D. et al., J. Exp. Med. (1996), Vol. 184, pp. 2007–2012); and cancer (Thomsen, L. L. et al., Cancer Res. (1997), Vol. 57, pp. 3300–3304).

The compounds of the current invention may also be useful for the management of male and female reproductive functions when used alone or combined with other drugs commonly used for these indications. Examples, without implied limitation, include: inhibition of fertilization, endometrial receptivity and implantation (alone or in combination with a progesterone antagonist); post-coital contraception (alone or in combination with a progesterone antagonist); induction of abortion (in combination with an antiprogestin and in further combination with a prostaglandin); control and management of labor and delivery; treatment of cervical incompetence (alone or in combination with progesterone or a progestin); treatment of endometriosis (alone or in combination with other drugs, including LHRH-agonists/antagonists, antiprogestins or progestins by either sequential application or by concomitant administration). See, for example, the following references: Chwalisz, K. et al., J. Soc. Gynecol. Invest. (1997), Vol. 4, No. 1 (Supplement), page 104a, which discusses the inhibition of fertilization, endometrial receptivity and implantation, or post-coital contraception, alone or in combination with a progesterone antagonist; Chwalisz, K. et al., Prenat. Neonat. Med. (1996), Vol. 1, pp. 292–329, which discusses the induction of abortion, in combination with an antiprogestin and in further combination with a prostaglandin, and the control and management of labor and delivery; and Chwalisz, K. et al., Hum. Reprod. (1997), vol. 12, pp. 101–109, which discusses the treatment of cervical incompetence, alone or in combination with progesterone or a progestin.

Those skilled in the art will also recognize that the compounds of the present invention include 1-substituted imidazoles. This class of compounds has previously been described as mechanism-based, heme-binding inhibitors of the cytochrome P450 family of enzymes (Maurice, M. et al., FASEB J. (1992), Vol. 6, pp. 752–758) in addition to NO synthesis (Chabin, R. N M. et al., Biochemistry (1996), Vol. 35, pp. 9567–9575). The compounds of the present invention may thus be useful as inhibitors of selected cytochrome P450 family members of therapeutic interest including, but not limited to, P450 enzymes involved in steroid and retinoid biosynthesis (Masamura et al., Breast Cancer Res. Treat. (1995), Vol. 33, pp. 19–26; Swart, P. et al., J. Clin. Endocrinol. Metab., Vol. 77, pp. 98–102; Docks, P. et al., Br. J. Dermatol. (1995), Vol. 133, pp. 426–432) and cholesterol biosynthesis (Burton, P. M. et al., Biochem. Pharmacol. (1995), Vol. 50, pp. 529–544; and Swinney, D. C. et al., Biochemistry (1994), Vol. 33, pp. 4702–4713). Imidazole-based compounds may also have antifungal activity (Aoyama, Y. et al., Biochem. Pharmacol. (1992), Vol. 44, pp. 1701–1705).

C. Testing of the Compounds of the Invention

Nitric oxide synthases are complex enzymes that catalyze the conversion of L-arginine to NO and citrulline. Catalysis proceeds through two successive oxidations of the guanidinium group of L-arginine.

A cell-based NOS assay employing the measurement of NO oxidation product, nitrite, in the conditioned medium of cultured cells was employed for the evaluation of the compounds of the invention in vitro. The murine monocytic cell lines RAW 264.7 and J774 are well documented as capable of producing >10 $\mu$M nitrite in response to immunostimulation. This in vitro assay is described in detail below in the Examples.

Various in vivo assays may be employed to determine the efficacy of the compounds of the invention in treating a condition resulting from an abnormality in NO production, such as arthritis. Such an assay is described in detail below in the Examples.

Those skilled in the art will also recognize that numerous assays for the activity of the NOS isoforms (iNOS, nNOS and eNOS) exist which can be used to evaluate the biological activity of the compounds of the current invention. These include assays for native NOS isoforms in tissues studied ex vivo (Mitchell et al., Br. J. Pharmacol. (1991), Vol. 104, pp. 289–291; Szabo et al., Br. J. Pharmacol. (1993), Vol. 108, pp. 786–792; Joly et al., Br. J. Pharmacol. (1995), Vol. 115, pp. 491–497) as well as primary cell cultures and cell lines (Forstermann et al., Eur. J. Pharmacol. (1992), Vol. 225, pp. 161–165; Radmoski et al., Cardiovasc. Res. (1993), Vol. 27, pp. 1380–1382; Wang et al., J. Pharmacol. Exp. Ther. (1994), Vol. 268, pp. 552–557). Those skilled in the art will also recognize that recombinant NOS enzymes can be expressed in heterologous cells by either transient transfection (Karlsen et al., Diabetes, (1995), Vol. 44, pp. 753–758), stable transfection (McMillan et al., Proc. Natl. Acad. Sci. (1992), Vol. 89, pp. 11141–11145; Sessa et al., J. Biol. Chem. (1995), Vol. 270, pp. 17641–17644) or via the use of lytic virus transfection (Busconi & Michel, Mol. Pharmacol. (1995), Vol. 47, pp. 655–659; List et al., Biochem. J. (1996), Vol. 315, pp. 57–63) using NOS cDNAs. Heterologous expression can be achieved in mammalian cells (McMillan et al., Proc. Natl. Acad. Sci. (1992), Vol. 89, pp. 11141–11145), insect cells (Busconi & Michel, Mol. Pharmacol. (1995), Vol. 47, pp. 655–659; List et al., Biochem. J. (1996), Vol. 315, pp. 57–63), yeast (Sari et al., Biochemistry (1996), Vol. 35, pp. 7204–7213) or bacteria (Roman et al., Proc. Natl. Acad. Sci. (1995), Vol. 92, pp. 8428–8432; Martasek et al., Biochem. Biophys. Res. Commun. (1996), Vol. 219, pp. 359–365). Any of these heterologous expression systems can be used to establish iNOS, nNOS and eNOS assay systems to evaluate the biological activity of the compounds of the present invention.

The P450 inhibitory activity of the compounds of the present invention can be assessed using appropriate assay systems specific for the P450 isoform of interest. Such assays are included in the references cited in the discussion of P450 family of enzymes in Paragraph B above. One additional example of mammalian cytochrome P450 isoform that may be inhibited by the compounds of the present invention is cytochrome P450 3A4 which can be assayed in a manner similar to the method described in Yamazaki et al., *Carcinogenesis* (1995), Vol. 16, pp. 2167–2170.

D. Administration of the Compounds of the Invention

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the invention as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. Preferably, the composition will be about 5% to 75% by weight of a compound(s) of the invention, or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of the invention, or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations, and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin, cellulose ether derivatives, and the like.

The compounds of the invention, or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of the invention (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a condition characterized by an abnormality in nitric oxide production in accordance with the teachings of this invention.

The compounds of the invention, or their pharmaceutically acceptable salts, are administered in a therapeutically effective amount which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease-states; and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

E. Preferred Embodiments

Of the compounds of the invention as set forth above in the Summary of the Invention, several groups of compounds are particularly preferred.

One preferred group of compounds are those compounds of formula (I):

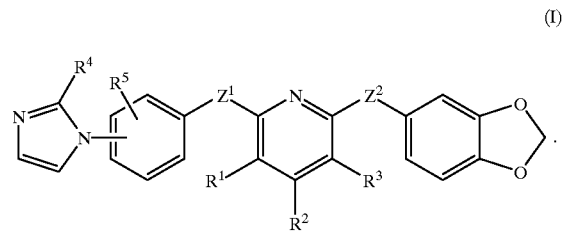

Of this group of compounds, a preferred subgroup of compounds is that subgroup wherein $Z^1$ is —O— or —(CH$_2$)$_m$—N(R$^7$) (where m is 0 to 2); $Z^2$ is —O—(CH$_2$)$_m$— (where m is 0 to 2), —S—(CH$_2$)$_m$— (where m is 0 to 2), or —N(R$^7$)—(CH$_2$)$_m$— (where m is 0 to 2); $R^1$ and $R^3$ are independently selected from the group consisting of hydrogen, halo, and alkyl; $R^2$ is hydrogen, alkyl, bromo, iodo, —N(R$^7$)—(CH$_2$)$_p$—N(R$^8$)R$^9$ (where p is 1 to 4), —(CH$_2$)$_q$—N(R$^7$)—CH$_2$—C(O)—OR$^8$ (where q is 0 to 3), 4-morpholinyl, 1-piperidinyl, 1-piperazinyl, or 1-pyrrolidinyl; $R^4$ is hydrogen or alkyl; $R^5$ is hydrogen, halo, haloalkyl, alkyl, nitro, —OR$^8$, —C(O)OR$^8$, —C(O)N(R$^8$)R$^9$, —N(R$^8$)R$^9$, —N(R$^8$)C(O)R$^8$, or —N(H)S(O)$_2$R$^{10}$;

each $R^7$ is hydrogen or alkyl; and each $R^8$ and $R^9$ is independently hydrogen or alkyl.

Of this subgroup of compounds, a preferred class of compounds is that class wherein $Z^1$ is —O—; $Z^2$ is —O—$(CH_2)_m$— (where m is 0 to 2), —S—$(CH_2)_m$— (where m is 0 to 2), or —$N(R^7)$—$(CH_2)_m$— (where m is 0 to 2); $R^1$ and $R^3$ are independently selected from the group consisting of hydrogen, chloro, and fluoro; $R^2$ is hydrogen, alkyl, bromo, iodo, —$N(R^7)$—$(CH_2)_p$—$N(R^8)R^9$ (where p is 1 to 4), —$(CH_2)_q$—$N(R^7)$—$CH_2$—C(O)—$OR^8$ (where q is 0 to 3), 4-morpholinyl, 1-piperidinyl, 1-piperazinyl, or 1-pyrrolidinyl; $R^4$ and $R^5$ are each independently hydrogen or alkyl; and each $R^7$, $R^8$ and $R^9$ is each independently hydrogen or alkyl.

Of this class of compounds, a preferred subclass of compounds is that subclass wherein $Z^1$ and $Z^2$ are both —O—; $R^1$ and $R^3$ are independently selected from the group consisting of hydrogen, chloro, and fluoro; $R^2$ is hydrogen, alkyl or —$N(R^7)$—$CH_2$—C(O)—$OR^8$; $R^4$ and $R^5$ are each independently hydrogen or alkyl; and each $R^7$ and $R^8$ is each independently hydrogen or alkyl.

Of this subclass of compounds, preferred compounds are those compounds wherein $R^1$, $R^2$, and $R^3$ are each hydrogen; $R^4$ is hydrogen; and $R^5$ is hydrogen or methyl.

Of these preferred compounds, the most preferred are the compounds selected from the group consisting of the following compounds:
2-(1,3-benzodioxol-5-yloxy)-6-[4-(1H-imidazol-1-yl)phenoxy]pyridine; and
2-(1,3-benzodioxol-5-yloxy)-6-[4-(1H-imidazol-1-yl)-2-methylphenoxy]pyridine; and
2-(1,3-benzodioxol-5-yloxy)-6-[3-(1H-imidazol-1-yl)phenoxy]pyridine.

Of the above-identified subclass of compounds, other preferred compounds are those compounds wherein $R^1$ and $R^3$ are independently fluoro or chloro; $R^2$ is hydrogen, alkyl or —$N(R^7)$—$CH_2$—C(O)—$OR^8$; $R^4$ is hydrogen; $R^5$ is hydrogen or alkyl; $R^7$ is methyl; and $R^8$ is hydrogen, methyl or ethyl.

Of these preferred compounds, the most preferred are the compounds selected from the group consisting of the following compounds:
2-(1,3-benzodioxol-5-yloxy)-3,5-difluoro-6-[4-(1H-imidazol-1-yl)phenoxy]-4-methylpyridine;
2-(1,3-benzodioxol-5-yloxy)-3,5-difluoro-6-[3-(1H-imidazol-1-yl)phenoxy]-4-methylpyridine; and
2-(1,3-benzodioxol-5-yloxy)-3,5-difluoro-6-[4-(1H-imidazol-1-yl)phenoxy]-4-[(N-methyl-N-((ethoxycarbonyl)methyl)amino]pyridine.

Of the class of compounds described above, a preferred subclass of compounds is that subclass wherein $Z^1$ is —O—; $Z^2$ is —$N(R^7)$—$(CH_2)_m$— (where m is 0 to 2); $R^1$ and $R^3$ are independently selected from the group consisting of hydrogen, chloro, and fluoro; $R^2$ is hydrogen, alkyl or —$N(R^7)$—$CH_2$—C(O)—$OR^8$; and $R^4$, $R^5$, $R^7$, and $R^8$ are each independently hydrogen or alkyl.

Of this subclass of compounds, preferred compounds are those compounds wherein $Z^1$ is —O—; $Z^2$ is —$N(R^7)$—$CH_2$—; $R^1$ and $R^3$ are independently selected from the group consisting of hydrogen, chloro, and fluoro; $R^2$ is hydrogen or methyl; $R^4$ and $R^5$ are each independently hydrogen or alkyl; and $R^7$ is hydrogen or alkyl.

Of these preferred compounds, the most preferred compound is 2-(4-(1H-imidazol-1-yl)phenoxy)-3,5-difluoro-4-methyl-6-[((1,3-benzodioxol-5-yl)methyl)amino]pyridine.

Another preferred group of compounds are those compounds of formula (II):

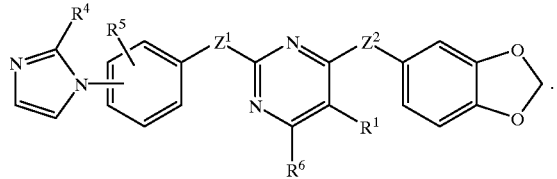

(II)

Of this group of compounds, a preferred subgroup of compounds is that subgroup wherein $Z^1$ is —O— or —$(CH_2)_m$—$N(R^7)$— (where m is 0 to 2); $Z^2$ is —O—$(CH_2)_m$— (where m is 0 to 2), —S—$(CH_2)_m$— (where m is 0 to 2), or —$N(R^7)$—$(CH_2)_m$— (where m is 0 to 2); $R^1$ is hydrogen, halo, or alkyl; $R^4$ is hydrogen or alkyl; $R^5$ is hydrogen, halo, haloalkyl, alkyl, nitro, —$OR^8$, —C(O)$OR^8$, C(O)$N(R^8)R^9$, —$N(R^8)R^9$, —$N(R^8)C(O)R^8$, or —$N(H)S(O)_2R^{10}$; $R^6$ is hydrogen, alkyl, aryl, aralkyl, halo, —$N(R^8)R^9$, —$N(R^7)$—$(CH_2)_p$—$N(R^8)R^9$ (where p is 1 to 4), —$(CH_2)_q$—$N(R^7)$—$CH_2$—C(O)$OR^8$ (where q is 0 to 3), 4-morpholinyl, 1-piperidinyl, 1-piperazinyl, or 1-pyrrolidinyl; each $R^7$ is independently hydrogen or alkyl; and each $R^8$ and $R^9$ is independently hydrogen or alkyl.

Of this subgroup of compounds, a preferred class of compounds is that class wherein $Z^1$ and $Z^2$ are both —O—; $R^1$ is hydrogen, chloro, or fluoro; $R^4$ is hydrogen or alkyl; $R^5$ is hydrogen, halo, haloalkyl or alkyl; $R^6$ is hydrogen, alkyl or —$(CH_2)_q$—$N(R^7)$—$CH_2$—C(O)—$OR^8$ (where q is 0 or 1); $R^7$ is hydrogen or alkyl; and $R^8$ is hydrogen or alkyl.

Of this class of compounds, a preferred subclass of compounds is that subclass wherein $R^4$ is hydrogen; $R^5$ is hydrogen, chloro, fluoro, trifluoromethyl or alkyl; $R^6$ is hydrogen, methyl, or —$CH_2$—$N(R^7)$—$CH_2$—C(O)—$OR^8$; $R^7$ is hydrogen or methyl; and $R^8$ is hydrogen or alkyl.

Of this subclass of compounds, preferred compounds are those compounds selected from the group consisting of the following compounds:
4-(1,3-benzodioxol-5-yloxy)-2-[4-(1H-imidazol-1-yl)phenoxy]pyrimidine;
4-(1,3-benzodioxol-5-yloxy)-2-[4-(1H-imidazol-1-yl)phenoxy]-6-methylpyrimidine;
4-(1,3-benzodioxol-5-yloxy)-2-[2-fluoro-4-(1H-imidazol-1-yl)phenoxy]-6-methylpyrimidine;
4-(1,3-benzodioxol-5-yloxy)-2-[3-chloro-4-(1H-imidazol-1-yl)phenoxy]-6-methylpyrimidine; and
4-(1,3-benzodioxol-5-yloxy)-2-[3-trifluoromethyl-4-(1H-imidazol-1-yl)phenoxy]-6-methylpyrimidine.

Another preferred group of compounds are those compounds of formula (III):

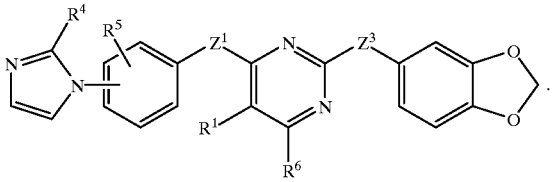

(III)

Of this group of compounds, a preferred subgroup of compounds is that subgroup wherein $Z^1$ is —O— or —$(CH_2)_m$—$N(R^7)$— (where m is 0 to 2); $Z^3$ is —O—$(CH_2)_m$— (where m is 0 to 2), —$(CH_2)_n$— (where n is 1 to 4), or —$N(R^7)$—$(CH_2)_m$— (where m is 0 to 2); $R^1$ is hydrogen, halo, or alkyl; $R^4$ is hydrogen or alkyl; $R^5$ is hydrogen, halo, haloalkyl, alkyl, nitro, —$OR^8$, —$C(O)OR^8$, —$C(O)N(R^8)R^9$, —$N(R^8)R^9$, —$N(R^8)C(O)R^8$, or —$N(H)S(O)_2R^{10}$; $R^6$ is hydrogen, alkyl, aryl, aralkyl, halo, —$N(R^8)R^9$, —$N(R^7)$—$(CH_2)_p$—$N(R^8)R^9$ (where p is 1 to 4), —$(CH_2)_q$—$N(R^7)$—$CH_2$—$C(O)OR^8$ (where q is 0 to 3), 4-morpholinyl, 1-piperidinyl, 1-piperazinyl, or 1-pyrrolidinyl; each $R^7$ is hydrogen or alkyl; and each $R^8$ and $R^9$ is independently hydrogen or alkyl.

Of this subgroup of compounds, a preferred class of compounds is that class wherein $Z^1$ is —O—; $Z^3$ is —O— or —$CH_2$—; $R^1$ is hydrogen, chloro, fluoro or methyl; $R^4$ and $R^5$ are independently hydrogen or alkyl; $R^6$ is hydrogen, alkyl, halo, 4-morpholinyl, —$N(R^7)$—$(CH_2)_p$—$N(R^8)R^9$ (where p is 1 to 4), or —$(CH_2)_q$—$N(R^7)$—$CH_2$—$C(O)$—$OR^8$ (where q is 0 to 3); and each $R^7$, $R^8$, and $R^9$ is hydrogen or alkyl.

Of this class of compounds, a preferred subclass of compounds is that subclass wherein $R^1$ is hydrogen or methyl; and $R^6$ is hydrogen, methyl, chloro, fluoro, 4-morpholinyl or —$N(R^7)$—$(CH_2)_m$—$N(R^8)R^9$ (where m is 1 to 4).

Of this subclass of compounds, preferred compounds are those compounds wherein $R^4$ is hydrogen; $R^5$ is hydrogen; $R^7$ is hydrogen or methyl; and $R^8$ and $R^9$ are independently hydrogen or methyl.

Of these preferred compounds, most preferred compounds are those compounds selected from the group consisting of the following compounds:

2-(1,3-benzodioxol-5-yloxy)-4-[4-(1H-imidazol-1-yl)phenoxy]pyrimidine;

2-(1,3-benzodioxol-5-yloxy)-4-[4-(1H-imidazol-1-yl)phenoxy]-5-methylpyrimidine;

2-[(1,3-benzodioxol-5-yl)methyl]-6-chloro-4-[4-(1H-imidazol-1-yl)phenoxy]pyrimidine;

2-[(1,3-benzodioxol-5-yl)methyl]-6-[3-(dimethylamino)propyl(methyl)amino]-4-[4-(1H-imidazol-1-yl)phenoxy]-5-methylpyrimidine; and 2-[(1,3-benzodioxol-5-yl)methyl]-4-[4-(1H-imidazol-1-yl)phenoxy]-6-(morpholin-4-yl)pyrimidine.

Another preferred group of compounds are compounds of formula (IV):

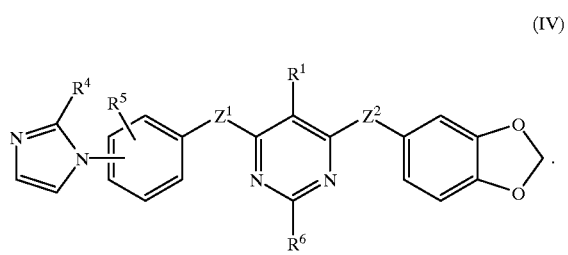

(IV)

Of this preferred group of compounds, a preferred subgroup of compounds is that subgroup wherein $Z^1$ is —O— or —$(CH_2)_m$—$N(R^7)$— (where m is 0 to 2); $Z^2$ is —O—$(CH_2)_m$— (where m is 0 to 2), —S—$(CH_2)_m$— (where m is 0 to 2), or —$N(R^7)$—$(CH_2)_m$— (where m is 0 to 2); $R^1$ is hydrogen, halo, or alkyl; $R^4$ is hydrogen or alkyl; $R^5$ is hydrogen, halo, haloalkyl, alkyl, nitro, —$OR^8$, —$C(O)OR^8$, —$C(O)N(R^8)R^9$, —$N(R^8)R^9$, —$N(R^8)C(O)R^8$, or —$N(H)S(O)_2R^{10}$; $R^6$ is hydrogen or alkyl; each $R^7$ is hydrogen or alkyl; and each $R^8$ and $R^9$ is independently hydrogen or alkyl.

Of this subgroup of compounds, a preferred class of compounds is that class wherein $Z^1$ and $Z^2$ are both —O—; $R^1$ is hydrogen, chloro, or fluoro; and $R^4$, $R^5$, and $R^6$ are independently hydrogen or alkyl.

Of this class of compounds, a preferred compound is 6-(1,3-benzodioxol-5-yloxy)-4-[4-(1H-imidazol-1-yl)phenoxy]pyrimidine.

F. Preparation of the Compounds of the Invention

As a matter of convenience, the following description of the preparation of the compounds of the invention is directed to the preparation of compounds of formula (I) and compounds of formula (III). It is understood, however, that similar synthetic methods may be used to prepare the corresponding compounds of formula (II) and (IV).

1. Preparation of Compounds of formula (C)

Compounds of formula (C) are intermediates used in the preparation of compounds of formula (I) as set forth above in the Summary of the Invention, and are prepared as described below in Reaction Scheme 1 where each X is independently fluoro or chloro, $R^1$ and $R^3$ are independently selected from the group consisting of hydrogen, halo, alkyl, haloalkyl, nitro, aralkoxy, —$OR^8$, —$R^{11}$—$OR^8$, —$N(R^8)R^9$, —$C(O)OR^8$, —$R^{11}$—$C(O)OR^8$, —$C(O)N(R^8)R^9$, —$R^{11}$—$C(O)N(R^8)R^9$, —$C(O)N(R^8)CH_2C(O)N(R^8)R^9$, —$N(R^8)C(O)N(R^8)R^9$, —$N(R^8)C(O)R^9$, —$N(R^8)S(O)_2R^{10}$, and —$N(R^8)C(O)N(R^8)$—$CH_2C(O)N(R^8)R^9$ (where each $R^8$, $R^9$, $R^{10}$ and $R^{11}$ are as described above in the Summary of the Invention); $R^2$ is hydrogen, bromo, iodo, alkyl, 4-morpholinyl, 1-piperidinyl, 1-piperazinyl, 1-pyrrolidinyl, —$N(R^7)$—$(CH_2)_p$—$N(R^8)R^9$ (where p is 1 to 4 and $R^7$, $R^8$ and $R^9$ are as described above in the Summary of the Invention) or —$(CH_2)_q$—$N(R^7)$—$CH_2$—$C(O)$—$OR^8$ (where q is 0 to 3 and $R^7$ and $R^8$ are as described above in the Summary of the Invention); and $Z^2$ is —O—$(CH_2)_m$— (where m is 0 to 2), —S—$(CH_2)_m$— (where m is 0 to 2), or —$N(R^7)$—$(CH_2)_m$— (where m is 0 to 2):

Reaction Scheme 1

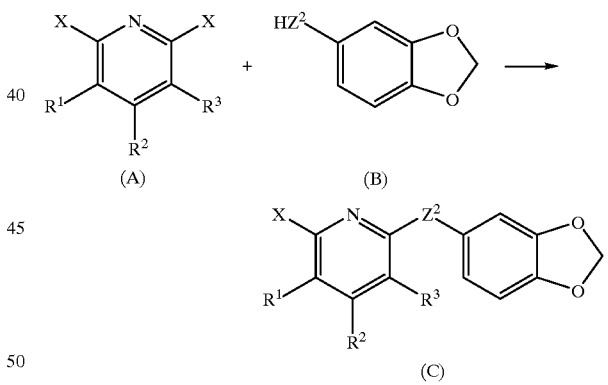

Compounds of formula (A) are commercially available, for example, from Aldrich Chemical Co., or can be prepared either according to methods known to those of ordinary skill in the art or according to the methods disclosed in U.S. Pat. No. 5,691,364 (Buckman et al.). Compounds of formula (B) are commercially available, for example, from Aldrich Chemical Co, or can be prepared according to methods known to those of ordinary skill in the art.

In general, compounds of formula (C) are prepared by first treating a solution of an equimolar amount of a compound of formula (A) and an equimolar amount of a compound of formula (B) in an aprotic solvent, such as dimethyl sulfoxide, with a base, preferably cesium carbonate. The resulting mixture is heated to between about 0° C. and about 60° C., preferably at about 50° C., for about 8 to about 18 hours, preferably for about 18 hours. The compound of formula (C) is then isolated from the reaction mixture by standard isolation techniques, such as extraction of the organic layer and in vacuo removal of the solvent.

In addition to the compounds of formula (A) as described above, similar compounds may be used in the above Reaction Scheme to produce corresponding compounds of formula (C). For example, compounds of formula (Aa), compounds of formula (Ab) and compounds of formula (Ac), as depicted below:

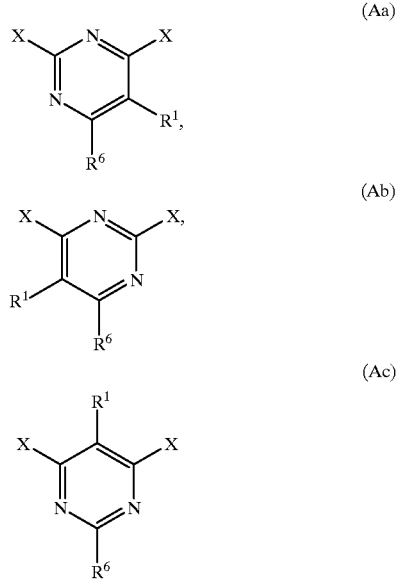

where each X and $R^1$ are the same as described above for compounds of formula (A) and $R^6$ is the same as described above in the Summary of the Invention, may be reacted with compounds of formula (B) as described above, to form the corresponding compounds of formula (C). Compounds of formula (Aa), compounds of formula (Ab) and compounds of formula (Ac) are commercially available, e.g., from Aldrich Chemical Co., or either may be prepared according to methods known to one of ordinary skill in the art or according to methods as described in U.S. Pat. No. 5,691,364 (Buckman et al.).

2. Preparation of compounds of formula (G)

Compounds of formula (G) are intermediates used in the preparation of compounds of formula (III) as set forth above in the Summary of the Invention, and are prepared as described below in Reaction Scheme 2 where $X^1$ and $X^2$ are the same and halo; $R^{1a}$ is hydrogen, alkyl, aralkoxy, —$OR^8$, —$R^{11}$—$OR^8$, —$C(O)OR^8$, or —$R^{11}$—$C(O)OR^8$; $R^{12}$ is alkyl or aralkyl; and $Z^3$ is —$(CH_2)_n$— (where n is 1 to 4):

Reaction Scheme 2

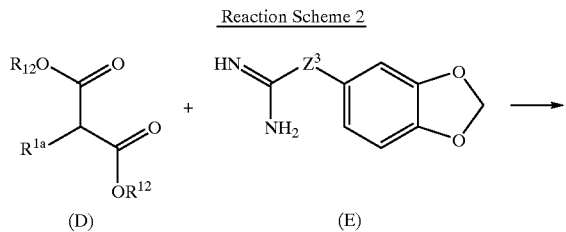

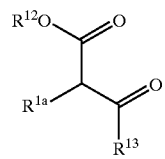

Compounds of formula (D) and compounds of formula (E) are commercially available, for example, from Aldrich Chemical Co., or may be prepared according to methods known to those of ordinary skill in the art.

In general, compounds of formula (G) are prepared by first dissolving a compound of formula (D) and an equimolar amount of a compound of formula (E) in a protic solvent, such as ethanol, in the presence of an excess amount of a metal alkoxide, such as sodium methoxide. The resulting mixture is allowed to reflux for between 4 and 6 hours, preferably for about 5 hours. The solvent is removed in vacuo and the resulting residue is dissolved in water, washed with ethyl acetate, treated with charcoal and acidified, for example, by the addition of a strong acid such as HCl. The compound of formula (F) is isolated from the residue by standard isolation techniques, such as filtration and removal of impurities.

A compound of formula (F) is then treated with an excess amount of a halogenating agent, such as phosphorus oxychloride, with a co-solvent, such as N,N-diethylaniline. The resulting mixture is heated to between about 35° C. and about 50° C., preferably to about 45° C., for about 2 to 6 hours, preferably for about 3 hours. The solvent is then removed in vacuo and the resulting residue is added to ice. The compound of formula (G) is isolated from the residue by standard isolation techniques, such as filtration and crystallization from an organic solvent, such as hexane.

Alternatively, compounds of the following formula:

where $R^{12}$ and $R^{1a}$ are defined above for the compounds of formula (D) and $R^{13}$ is hydrogen, alkyl, aryl or aralkyl, may be treated with compounds of formula (E), as described above, under standard primary synthesis conditions of pyrimidines known to those of ordinary skill in the art to form corresponding mono-hydroxy compounds of formula (F). These compounds may then be treated under similar halogenating conditions as described above for compounds of formula (F) in the foregoing Reaction Scheme to form corresponding compounds of formula (G) where $X^1$ is halo and $X^2$ is hydrogen, alkyl, aryl or aralkyl.

Alternatively, compounds of formula (G), as described above where X² is halo, may be treated with a hydrogenating agent under standard hydrogenation conditions known to those of ordinary skill in the art to form the corresponding compounds of formula (G) where X² is hydrogen.

Alternatively, compounds of formula (F) where $R^{1a}$ is hydrogen may be treated with a nitrating agent under standard nitration conditions to form compounds of formula (F) where $R^{1a}$ is nitro. These compounds can then be treated in a similar manner as compounds of formula (F) in Reaction Scheme 2 above to form compounds of formula (G) where $R^{1a}$ is nitro, when can then be treated in a similar manner as described below in Reaction Scheme 4 to form compounds of formula (IIIa) and formula (IIIb) where $R^{1a}$ is nitro. These compounds can then be treated under standard reduction conditions to form compounds of formula (IIIa) and formula (IIIb) where $R^{1a}$ is —N(R⁸)R⁹ where R⁸ and R⁹ are described above in the Summary of the Invention.

3. Preparation of compounds of formula (Ia)

Compounds of formula (Ia) are compounds of formula (I) as set forth above in the Summary of the Invention, and are prepared as described below in Reaction Scheme 3 wherein X is fluoro or chloro; R¹ and R³ are independently selected from the group consisting of hydrogen, halo, alkyl, haloalkyl, nitro, aralkoxy, —OR⁸, —R¹¹—OR⁸, —N(R⁸)R⁹, —C(O)OR⁸, —R¹¹—C(O)OR⁸, —C(O)N(R⁸)R⁹, —R¹¹—C(O)N(R⁸)R⁹, —C(O)N(R⁸)CH₂C(O)N(R⁸)R⁹, —N(R⁸)C(O)N(R⁸)R⁹, —N(R⁸)C(O)R⁹, —N(R⁸)S(O)₂R¹⁰, and —N(R⁸)C(O)N(R⁸)—CH₂C(O)N(R⁸)R⁹ (where each R⁸, R⁹, R¹⁰ and R¹¹ are as described above in the Summary of the Invention); R² is hydrogen, bromo, iodo, alkyl, 4-morpholinyl, 1-piperidinyl, 1-piperazinyl, or 1-pyrrolidinyl, —N(R⁷)—(CH₂)$_p$—N(R⁸)R⁹ (where p is 1 to 4 and R⁷, R⁸ and R⁹ are as described above in the Summary of the Invention) or —(CH₂)$_q$—N(R⁷)—CH₂—C(O)—OR₈ (where q is 0 to 3 and R⁷ and R⁸ are as described above in the Summary of the Invention); R⁴ is hydrogen or alkyl; R⁵ is hydrogen, halo, haloalkyl, alkyl, nitro, —OR⁸, —C(O)OR⁸, —C(O)N(R⁸)R⁹, —N(R⁸)R⁹, —N(R⁸)C(O)R⁸, or —N(H)S(O)₂R¹⁰; Z¹ is —(CH₂)$_m$—O— (where m is 0 to 2), —(CH₂)$_m$—S— (where m is 0 to 2), or —(CH₂)$_m$—N(R⁷)— (where m is 0 to 2); and Z² is —O—(CH₂)$_m$— (where m is 0 to 2), —S—(CH₂)$_m$— (where m is 0 to 2), or —N(R⁷)—(CH₂)$_m$— (where m is 0 to 2):

Reaction Scheme 3

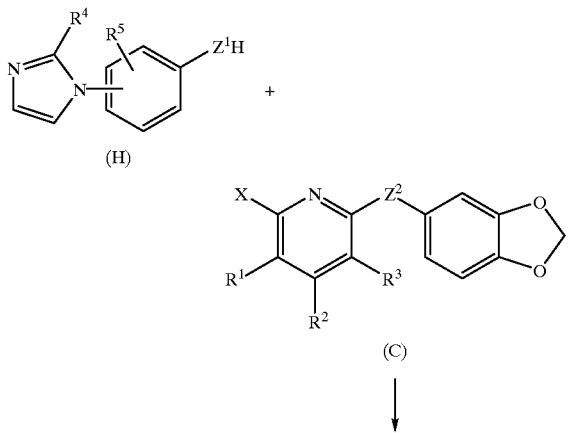

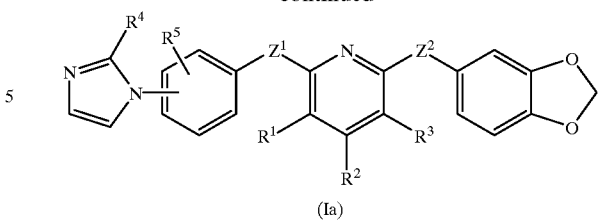

Compounds of formula (H) are commercially available or may be prepared according to methods known to those of ordinary skill in the art. Compounds of formula (C) are prepared according to methods described herein.

In general, compounds of formula (Ia) are prepared by treating a compound of formula (H) in an aprotic solvent, such as dimethyl sulfoxide, with an equimolar amount of a compound of formula (C) in the presence of a base, such as cesium carbonate. The mixture is heated to between 40° C. and 100° C., preferably to about 90° C., for a period of time sufficient to complete the reaction, preferably for about 18 hours. The compound of formula (Ia) is then isolated from the reaction mixture by standard isolation techniques, such as extraction, in vacuo removal of the solvent and flash chromatography.

In a similar manner, other compounds of the invention may be prepared. For example, compounds of formula (Aa), formula (Ab) and formula (Ac), as depicted above, may be used to prepare the corresponding compounds of formula (C), as described above, which can then be treated with compounds of formula (H), as described above, to prepare compounds of formula (II), formula (III) and formula (IV) as described above in the Summary of the invention.

4. Preparation of compounds of formula (IIIa)

Compounds of formula (IIIa) are compounds of formula (III) as set forth above in the Summary of the Invention, and are prepared as described below in Reaction Scheme 4 wherein X¹ and X² are the same and halo; $R^{1a}$ is hydrogen, alkyl, nitro, aralkoxy, —OR⁸, —R¹¹—OR⁸, —N(R⁸)R⁹, —C(O)OR⁸, —R¹¹—C(O)OR⁸, or —N(R⁸)S(O)₂R¹⁰; R⁴ is hydrogen or alkyl; R⁵ is hydrogen, halo, haloalkyl, alkyl, nitro, —OR⁸, —C(O)OR⁸, —C(O)N(R⁸)R⁹, —N(R⁸)R⁹, —N(R⁸)C(O)R⁸, or —N(H)S(O)₂R¹⁰; $R^{6a}$ is hydrogen, alkyl, aryl, aralkyl, halo, —N(R⁸)R⁹, —N(R⁷)—(CH₂)$_p$—N(R⁸)R⁹ (where p is 1 to 4), —(CH₂)$_q$—N(R⁷)—CH₂—C(O)OR⁸ (where q is 0 to 3), 4-morpholinyl, 1-piperidinyl, 1-piperazinyl, or 1-pyrrolidinyl (where each p, q, R⁸, R⁹ and R¹⁰ are as described above in the Summary of the invention); Z¹ is —(CH₂)$_m$—O— (where m is 0 to 2), —(CH₂)$_m$—S— (where m is 0 to 2), or —(CH₂)$_m$—N(R⁷)— (where m is 0 to 2); and Z³ is —(CH₂)$_n$— (where n is 1 to 4), —O—(CH₂)$_m$— (where m is 0 to 2), —S—(CH₂)$_m$— (where m is 0 to 2), or —N(R⁷)—(CH₂)$_m$— (where m is 0 to 2);

Reaction Scheme 4

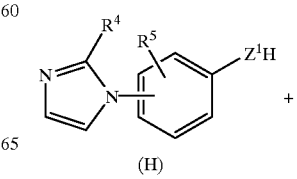

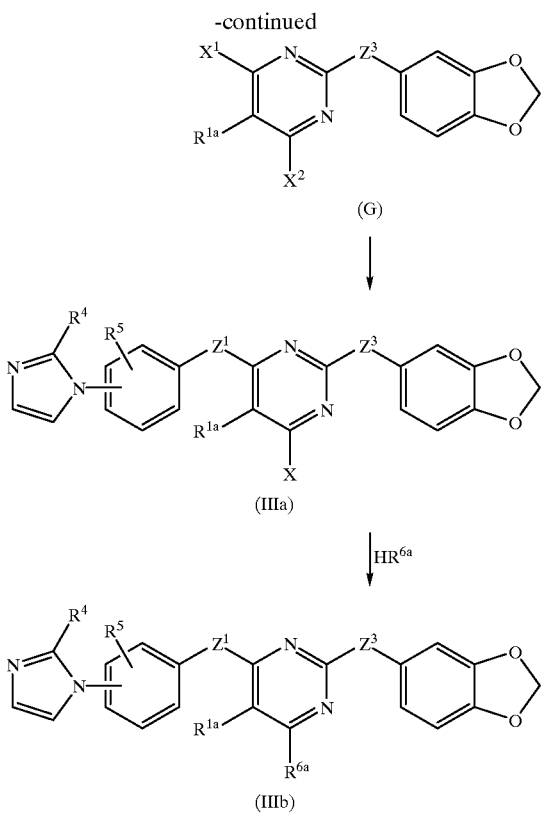

Compounds of formula (H) are commercially available or may be prepared according to methods known to those skilled in the art. Compounds of formula (G) are prepared according to methods disclosed herein.

In general, compounds of formula (IIIa) are prepared by treating a compound of formula (H) with a compound of formula (G) in a similar manner as described above for the treatment of a compound of formula (H) with a compound of formula (C) to prepare a compound of formula (Ia). The resulting compound of formula (IIIa) is treated with a compound of formula HR$^{6a}$ (where R$^{6a}$ is as described above) in an aprotic solvent, such as dimethyl sulfoxide. The resulting mixture is heated to between about 40° C. and about 100° C., preferably to about 40° C., for about 12 to about 24 hours, preferably for about 18 hours. The compound of formula (IIIb) is then isolated from the reaction mixture by standard isolation techniques, such as extraction, in vacuo removal of the solvent and crystallization.

Alternatively, compounds of formula (G) where X$^1$ is halo and X$^2$ is hydrogen or alkyl, prepared as described above in Reaction Scheme 2, may be treated with compounds of formula (H), under similar conditions as described above, to prepared compounds of formula (III) where R$^6$ is hydrogen or alkyl.

Compounds of formula (IIIa) and formula (IIIb) where R$^{1a}$ is hydroxy or alkyl may be treated with an appropriate halogenating agent under standard conditions to form corresponding compounds of formula (IIIa) and formula (IIIb) where R$^{1a}$ is halo or haloalkyl, respectively. Alternatively, compounds of formula (IIIa) and formula (IIIb) where R$^{1a}$ is —N(R$^8$)R$^9$—, —C(O)OR$^8$, —R$^{11}$—C(O)OR$^8$ may be treated under standard alkylation, acylation or condensation conditions known to those of ordinary skill in the art to form compounds of formula (IIIa) and formula (IIIb) where R$^{1a}$ is —C(O)N(R$^8$)R$^9$, —R$^{11}$—C(O)N(R$^8$)R$^9$, —C(O)N(R$^8$)CH$_2$C(O)N(R$^8$)R$^9$, —N(R$^8$)C(O)N(R$^8$)R$^9$ and —N(R$^8$)C(O)R$^9$.

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques.

The following specific preparations and examples are provided as a guide to assist in the practice of the invention, and are not intended as a limitation on the scope of the invention.

PREPARATION 1

Compounds of Formula (C)

A. To DMSO (5 mL) was added 5-hydroxy-1,3-benzodioxolane (1.09 g, 7.9 mmol), difluoropyridine (0.72 mL, 7.9 mmol), and cesium carbonate (2.62 g, 8.0 mmol). After heating at 50° C. for 18 hours, the reaction was partitioned with water and ethyl acetate. The organic layer was washed with water, brine, and dried (Na$_2$SO$_4$). The solvent was removed to give 2-(1,3-benzodioxol-5-yloxy)-6-fluoropyridine.

B. In a similar manner, the following compounds were prepared:
2-(1,3-benzodioxol-5-yloxy)-3,5,6-trifluoro-4-methylpyridine;
2-(1,3-benzodioxol-5-yloxy)-4-chloropyrimidine;
2-(1,3-benzodioxol-5-yloxy)-4-chloro-6-methylpyrimidine;
2-(1,3-benzodioxol-5-yloxy)-4-chloro-5-methylpyrimidine;
4-[(N-methyl-N-((ethoxycarbonyl)methyl)amino]-2-(1,3-benzodioxol-5-yloxy)-3,5,6-trifluoropyridine.

C. In a similar manner, the following compounds are prepared:
2-(1,3-benzodioxol-5-yl)methoxy-3,5,6-trifluoro-4-methylpyridine;
2-(1,3-benzodioxol-5-yl)methylthio-3,5,6-trifluoro-4-ethylpyridine;
2-[N-(1,3-benzodioxol-5-yl)amino]-3,5,6-trichloro-4-methylpyridine;
2-[N-((1,3-benzodioxol-5-yl)methyl)amino]-3,5,6-trifluoro-4-methylpyridine;
2-(1,3-benzodioxol-5-yloxy)-5,6-dichloropyridine;
2-(1,3-benzodioxol-5-yloxy)-6-fluoro-5-methylpyridine;
2-(1,3-benzodioxol-5-yloxy)-3,5-diethyl-6-fluoropyridine;
2-(1,3-benzodioxol-5-yloxy)-3,5-di(trifluoromethyl)-6-fluoropyridine;
2-(1,3-benzodioxol-5-yloxy)-3,5-di(methoxy)-6-fluoropyridine;
2-(1,3-benzodioxol-5-yloxy)-6-chloro-5-nitropyridine;
2-(1,3-benzodioxol-5-yloxy)-3,5,6-trifluoro-4-bromopyridine;
2-(1,3-benzodioxol-5-yloxy)-6-fluoro-5-methoxycarbonylpyridine;
2-(1,3-benzodioxol-5-yloxy)-6-fluoro-5-methoxycarbonylmethylpyridine;
2-(1,3-benzodioxol-5-yloxy)-6-fluoro-5-aminocarbonylpyridine;
2-(1,3-benzodioxol-5-yloxy)-6-fluoro-5-(aminocarbonyl)methylpyridine;
2-(1,3-benzodioxol-5-yloxy)-6-fluoro-5-[(N-((aminocarbonyl)methyl)amino)carbonyl]pyridine;
2-(1,3-benzodioxol-5-yloxy)-6-fluoro-5-ureidopyridine;
2-(1,3-benzodioxol-5-yloxy)-6-fluoro-5-formamidopyridine;
2-(1,3-benzodioxol-5-yloxy)-6-fluoro-5-(phenylsulfonyl)aminopyridine;
2-(1,3-benzodioxol-5-yloxy)-6-fluoro-5-[N'-(aminocarbonylmethyl)ureido]pyridine;

4-(1,3-benzodioxol-5-yloxy)-2,6-dichloro-5-methylpyrimidine;

4-(1,3-benzodioxol-5-yl)methoxy-2,6-dichloro-5-methylpyrimidine;

4-(1,3-benzodioxol-5-yl)methylthio-2,6-dichloro-5-methylpyrimidine;

4-[N-(1,3-benzodioxol-5-yl)amino]-2,6-dichloro-5-methylpyrimidine;

4-[N-((1,3-benzodioxol-5-yl)methyl)amino]-2,6-dichloro-5-methylpyrimidine;

4-(1,3-benzodioxol-5-yloxy)-2-fluoro-5,6-dimethylpyrimidine;

4-(1,3-benzodioxol-5-yloxy)-2,6-dichloro-5-methylpyrimidine;

2-(1,3-benzodioxol-5-yloxy)-4,6-dichloro-5-methylpyrimidine;

2-(1,3-benzodioxol-5-yl)methoxy-4,6-dichloro-5-methylpyrimidine;

2-(1,3-benzodioxol-5-yl)methylthio-4,6-dichloro-5-methylpyrimidine;

2-[(1,3-benzodioxol-5-yl)amino]-4,6-dichloro-5-methylpyrimidine;

2-[((1,3-benzodioxol-5-yl)methyl)amino]-4,6-dichloro-5-methylpyrimidine;

2-(1,3-benzodioxol-5-yloxy)-4-chloro-5,6-dimethylpyrimidine; and 2-(1,3-benzodioxol-5-yloxy)-4,6-dichloro-5-methylpyrimidine.

PREPARATION 2

Compounds of Formula (F)

A. To ethanol (350 mL) was added 5-(amidino)methyl-1,3-benzodioxolane (50 g, 0.23 mol), diethyl methylmalonate (50 mL), and sodium methoxide (120 mL of 25 wt % in methanol). After refluxing for 5 hours, the solvent was removed in vacuo. The residue was dissolved in water, washed with ethyl acetate, treated with charcoal, and acidified with 6 N HCl. The resulting solid was collected by filtration, washed with water, $CH_3CN$ and ethyl ether to give 54 g of 2-[(1,3-benzodioxol-5-yl)methyl]-4,6-dihydroxy-5-methylpyrimidine.

B. In a similar manner, the following compound was prepared:

2-[(1,3-benzodioxol-5-yl)methyl]-4,6-dihydroxypyrimidine.

C. In a similar manner, the following compounds of formula (F) are prepared:

2-[(1,3-benzodioxol-5-yl]methyl]-4,6-dihydroxy-5-ethylpyrimidine;

2-[(1,3-benzodioxol-5-yl]methyl]-4,6-dihydroxy-5-(phenyl)methoxypyrimidine;

2-[(1,3-benzodioxol-5-yl]methyl]-4,6-dihydroxy-5-methoxypyrimidine;

2-[(1,3-benzodioxol-5-yl]methyl]-4,6-dihydroxy-5-(methoxy)methylpyrimidine;

2-[(1,3-benzodioxol-5-yl]methyl]-4,6-dihydroxy-5-(methoxycarbonyl)pyrimidine;

2-[(1,3-benzodioxol-5-yl]methyl]-4,6-dihydroxy-5-(methoxycarbonyl)methylpyrimidine;

2-[(1,3-benzodioxol-5-yl]methyl]-6-hydroxy-5-ethylpyrimidine;

2-[(1,3-benzodioxol-5-yl]methyl]-6-hydroxy-5-(phenyl)methoxypyrimidine;

2-[(1,3-benzodioxol-5-yl]methyl]-6-hydroxy-5-methoxypyrimidine;

2-[(1,3-benzodioxol-5-yl)methyl]-6-hydroxy-5-(methoxy)methylpyrimidine;

2-[(1,3-benzodioxol-5-yl]methyl]-6-hydroxy-5-(methoxycarbonyl)pyrimidine; and

2-[(1,3-benzodioxol-5-yl]methyl]-6-hydroxy-5-(methoxycarbonyl)methylpyrimidine.

D. Alternatively, compounds of formula (F) where $R^{1a}$ is hydrogen are nitrated under standard nitrating conditions to produce the following compounds:

2-[(1,3-benzodioxol-5-yl]methyl]-4,6-dihydroxy-5-nitropyrimidine; and

2-[(1,3-benzodioxol-5-yl]methyl]-6-hydroxy-5-nitropyrimidine.

PREPARATION 3

Compounds of formula (G)

A. To phosphorous oxychloride (300 mL) was added 2-[(1,3-benzodioxol-5-yl)methyl]-4,6-dihydroxy-5-methylpyrimidine (54 g) and N,N-diethylaniline (65 mL). After heating at 45° C. for 3 hours, the solvent was removed in vacuo and the residue was added to ice. The solids were collected by filtration, dissolved in $CH_2Cl_2$, washed with aqueous $K_2CO_3$, dried ($MgSO_4$), and the solvent was removed in vacuo. The residue was crystallized from hexanes to give 45 g of 2-[(1,3-benzodioxol-5-yl)methyl]-4,6-dichloro-5-methylpyrimidine.

B. In a similar manner, the following compound was made:

2-[(1,3-benzodioxol-5-yl)methyl]-4,6-dichloropyrimidine.

C. In a similar manner, the following compounds of formula (G) are made:

2-[(1,3-benzodioxol-5-yl]methyl]-4,6-dichloro-5-ethylpyrimidine;

2-[(1,3-benzodioxol-5-yl]methyl]-4,6-dichloro-5-(phenyl)methoxypyrimidine;

2-[(1,3-benzodioxol-5-yl]methyl]-4,6-dichloro-5-methoxypyrimidine;

2-[(1,3-benzodioxol-5-yl)methyl]-4,6-dichloro-5-(methoxy)methylpyrimidine;

2-[(1,3-benzodioxol-5-yl]methyl]-4,6-dichloro-5-(methoxycarbonyl)pyrimidine;

2-[(1,3-benzodioxol-5-yl]methyl]-4,6-dichloro-5-(methoxycarbonyl)methylpyrimidine;

2-[(1,3-benzodioxol-5-yl]methyl]-6-chloro-5-ethylpyrimidine;

2-[(1,3-benzodioxol-5-yl]methyl]-6-chloro-5-(phenyl)methoxypyrimidine;

2-[(1,3-benzodioxol-5-yl]methyl]-6-chloro-5-methoxypyrimidine;

2-[(1,3-benzodioxol-5-yl)methyl]-6-chloro-5-(methoxy)methylpyrimidine;

2-[(1,3-benzodioxol-5-yl]methyl]-6-chloro-5-(methoxycarbonyl)pyrimidine; and

2-[(1,3-benzodioxol-5-yl]methyl]-6-chloro-5-(methoxycarbonyl)methylpyrimidine.

EXAMPLE 1

Compounds of the Invention

A. To DMSO (5 mL) was added 2-(1,3-benzodioxol-5-yloxy)-6-fluoropyridine (1.3 g, 5.3 mmol), 1-(4-hydroxyphenyl)imidazole (0.92 mL, 5.8 mmol), and cesium carbonate (1.82 g, 5.6 mmol). After heating at 90° C. for 18 hour, the reaction was partitioned with water and ethyl acetate. The organic layer was washed with water and brine, dried ($Na_2SO_4$) and the solvent was removed in vacuo. The residue was chromatographed on silica with ethyl acetate/ hexane to get 1.1 g of 2-(1,3-benzodioxol-5-yloxy)-6-[4-(1H-imidazol-1-yl)phenoxy]pyridine; NMR (CDCl$_3$) δ 7.8 (s, 1H), 7.7 (t, 1H), 7.35 (d, 2H), 7.2 (m, 3H), 6.75 (d, 1H), 6.6 (m, 3H), 6.55 (m, 2H), 5.9 (s, 2H) ppm.

B. In a similar manner, the following compounds were prepared:

2-(1,3-benzodioxol-5-yloxy)-6-[4-(1H-imidazol-1-yl)-2-methylphenoxy]pyridine; NMR (CDCl$_3$) δ 7.8 (s, 1H), 7.65 (t, 1H), 7.2 (m, 4H), 6.7 (d, 1H), 6.5 (m, 3H), 5.85 (s, 2H), 2.2 (s, 3H) ppm;

2-[(1,3-benzodioxol-5-yl)methyl]-6-chloro-4-[(1H-imidazol-1-yl)phenoxy]-5-methylpyrimidine;

2-[(1,3-benzodioxol-5-yl)methyl]-6-chloro-4-[(1H-imidazol-1-yl)phenoxy]pyrimidine;

2-(1,3-benzodioxol-5-yloxy)-3,5-dichloro-6-[4-(1H-imidazol-1-yl)phenoxy]-4-[(N-methyl-N-((ethoxycarbonyl)methyl)amino)methyl]pyridine;

4-(1,3-benzodioxol-5-yloxy)-2-[4-(1H-imidazol-1-yl)phenoxy]pyrimidine; NMR (DMSO-d$_6$) δ 8.4 (d, 1H), 8.2 (s, 1H), 7.7 (t, 1H), 7.6 (d, 2H), 7.3 (d, 2H), 7.1 (s, 1H), 6.9 (d, 1H), 6.85 (d, 1H), 6.75 (d, 1H), 6.65 (dd, 1H), 6.0 (s, 2H) ppm;

4-(1,3-benzodioxol-5-yloxy)-2-[3-(1H-imidazol-1-yl)phenoxy]-6-methylpyrimidine;

4-(1,3-benzodioxol-5-yloxy)-2-[4-(1H-imidazol-1-yl)phenoxy]-6-methylpyrimidine; NMR (CDCl$_3$) δ 7.8 (s, 1H), 7.3 (d, 2H), 7.25 (m, 3H), 7.2 (s, 1H), 6.7 (d, 1H), 6.55 (d, 1H), 6.5 (dd, 1H), 6.35 (s, 1H), 5.9 (s, 2H), 2.4 (s, 3H) ppm;

2-(1,3-benzodioxol-5-yloxy)-4-[4-(1H-imidazol-1-yl)phenoxy]pyrimidine; NMR (DMSO-d$_6$) δ 8.4 (d, 1H), 8.25 (s, 1H), 7.7 (t, 1H), 7.68 (d, 2H), 7.35 (d, 2H), 7.1 (s, 1H), 6.8 (d, 2H), 6.75 (d, 1H), 6.55 (dd, 1H), 5.95 (s, 2H) ppm;

2-(1,3-benzodioxol-5-yloxy)-4-[4-(1H-imidazol-1-yl)phenoxy]-5-methylpyrimidine; NMR (CDCl$_3$) δ 8.1 (s, 1H), 7.8 (s, 1H), 7.3 (d, 2H), 7.25 (m, 1H), 7.2 (s, 1H), 7.18 (m, 2H), 6.8 (d, 1H), 6.6 (d, 1H), 6.55 (dd, 1H), 5.9 (s, 2H), 2.2 (s, 3H) ppm;

2-(1,3-benzodioxol-5-yloxy)-3,5-difluoro-6-[4-(1H-imidazol-1-yl)phenoxy]-4-methylpyridine; NMR (CDCl$_3$) δ 7.81 (s, 1H), 7.27 (m, 4H), 7.13 (d, 2H), 6.65 (d, 1H), 6.48 (m, 2H), 5.81 (s, 2H), 2.38 (s, 3H) ppm;

2-(1,3-benzodioxol-5-yloxy)-3,5-difluoro-6-[3-(1H-imidazol-1-yl)phenoxy]-4-methylpyridine;

2-(1,3-benzodioxol-5-yloxy)-6-[3-(1H-imidazol-1-yl)phenoxy]pyridine;

2-(1,3-benzodioxol-5-yloxy)-3,5-difluoro-6-[4-(1H-imidazol-1-yl)phenoxy]-4-[(N-methyl-N-((ethoxycarbonyl)methyl)amino]pyridine; NMR (CDCl$_3$) δ 7.8 (s, 1H), 7.25 (s, 1H), 7.2 (m, 2H), 7.15 (s, 1H), 7.1 (m, 2H), 6.8 (d, 1H), 6.5 (d, 1H), 6.4 (dd, 1H), 5.9 (s, 2H), 4.2 (q, 2H), 4.1 (s, 2H), 3.2 (s, 3H), 1.3 (t, 3H) ppm;

4-(1,3-benzodioxol-5-yloxy)-2-[2-fluoro-4-(1H-imidazol-1-yl)phenoxy]-6-methylpyrimidine; NMR (CDCl$_3$) δ 7.87 (s, 1H), 7.31 (d, 1H), 7.26–7.24 (m, 4H), 6.73 (d, 1H), 6.57 (d, 1H), 6.52 (dd, 2H), 6.42 (s, 1H), 5.87 (s, 2H), 2.42 (s, 3H) ppm;

2-(1,3-benzodioxol-5-yloxy)-3,5-dichloro-6-[4-(1H-imidazol-1-yl)phenoxy]-4-[(N-methyl-N-((carboxy)methyl)amino]pyridine;

2-(1,3-benzodioxol-5-yloxy)-3,5-dichloro-6-[4-(1H-imidazol-1-yl)phenoxy]-4-[(N-methyl-N-((ethoxycarbonyl)methyl)amino]pyridine;

6-(1,3-benzodioxol-5-yloxy)-4-[4-(1H-imidazol-1-yl)phenoxy]pyrimidine;

2-(4-(1H-imidazol-1-yl)phenoxy)-3,5-difluoro-4-methyl-6-[((1,3-benzodioxol-5-yl)methyl)amino]pyridine;

4-(1,3-benzodioxol-5-yloxy)-2-[3-chloro-4-(1H-imidazol-1-yl)phenoxy]-6-methylpyrimidine; NMR (CDCl$_3$) δ 7.84 (s, 1H), 7.46 (dd, 1H), 7.28–7.26 (m, 3H), 7.23 (s, 1H), 6.70 (d, 1H), 6.56 (d, 1H), 6.51 dd, 1H), 6.40 (s, 1H), 5.85 (s, 2H), 2.42 (s, 3H) ppm; and 4-(1,3-benzodioxol-5-yloxy)-2-[3-trifluoromethyl-4-(1H-imidazol-1-yl)phenoxy]-6-methylpyrimidine; NMR (CDCl$_3$) δ 7.87 (s, 1H), 7.66 (d, 1H), 7.54 (dd, 1H), 7.33 (d, 1H), 7.30 (s, 1H), 7.26 (s, 1H), 6.73 (d, 1H), 6.54 (d, 1H), 6.50 (dd, 1H), 6.39 (s, 1H), 5.89 (s, 2H), 2.42 (s, 3H) ppm.

C. In a similar manner, the following compounds of the invention are prepared:

2-(1,3-benzodioxol-5-yl)methoxy-3,5-difluoro-4-methyl-6-[4-(1H-imidazol-1-yl)phenoxy]pyridine;

2-(1,3-benzodioxol-5-yl)methylthio-3,5-difluoro-4-ethyl-6-[4-(1H-imidazol-1-yl)phenoxy]pyridine;

2-[N-(1,3-benzodioxol-5-yl)amino]-3,5-dichloro-4-methyl-6-[4-(1H-imidazol-1-yl)phenoxy]pyridine;

2-[N-((1,3-benzodioxol-5-yl)methyl)amino]-3,5-difluoro-4-methyl-6-[4-(1H-imidazol-1-yl)phenoxy]pyridine;

2-(1,3-benzodioxol-5-yloxy)-5-chloro-6-[4-(1H-imidazol-1-yl)phenoxy]pyridine;

2-(1,3-benzodioxol-5-yloxy)-5-methyl-6-[4-(1H-imidazol-1-yl)phenoxy]pyridine;

2-(1,3-benzodioxol-5-yloxy)-3,5-diethyl-6-[4-(1H-imidazol-1-yl)phenoxy]pyridine;

2-(1,3-benzodioxol-5-yloxy)-3,5-di(trifluoromethyl)-6-[4-(1H-imidazol-1-yl)phenoxy]pyridine;

2-(1,3-benzodioxol-5-yloxy)-3,5-di(methoxy)-6-[4-(1H-imidazol-1-yl)phenoxy]pyridine;

2-(1,3-benzodioxol-5-yloxy)-5-nitro-6-[4-(1H-imidazol-1-yl)phenoxy]pyridine;

2-(1,3-benzodioxol-5-yloxy)-3,5-difluoro-4-bromo-6-[4-(1H-imidazol-1-yl)phenoxy]pyridine;

2-(1,3-benzodioxol-5-yloxy)-5-methoxycarbonyl-6-[4-(1H-imidazol-1-yl)phenoxy]pyridine;

2-(1,3-benzodioxol-5-yloxy)-5-methoxycarbonylmethyl-6-[4-(1H-imidazol-1-yl)phenoxy]pyridine;

2-(1,3-benzodioxol-5-yloxy)-5-aminocarbonyl-6-[4-(1H-imidazol-1-yl)phenoxy]pyridine;

2-(1,3-benzodioxol-5-yloxy)-5-(aminocarbonyl)methyl-6-[4-(1H-imidazol-1-yl)phenoxy]pyridine;

2-(1,3-benzodioxol-5-yloxy)-5-[(N-((aminocarbonyl)methyl)amino)carbonyl]-6-[4-(1H-imidazol-1-yl)phenoxy]pyridine;

2-(1,3-benzodioxol-5-yloxy)-5-ureido-6-[4-(1H-imidazol-1-yl)phenoxy]pyridine;

2-(1,3-benzodioxol-5-yloxy)-5-formamido-6-[4-(1H-imidazol-1-yl)phenoxy]pyridine;

2-(1,3-benzodioxol-5-yloxy)-5-(phenylsulfonyl)amino-6-[4-(1H-imidazol-1-yl)phenoxy]pyridine;

2-(1,3-benzodioxol-5-yloxy)-5-[N'-(aminocarbonylmethyl)ureido]-6-[4-(1H-imidazol-1-yl)phenoxy]pyridine;

4-(1,3-benzodioxol-5-yloxy)-6-chloro-5-methyl-2-[4-(1H-imidazol-1-yl)phenoxy]pyrimidine;

4-(1,3-benzodioxol-5-yl)methoxy-6-chloro-5-methyl-2-[4-(1H-imidazol-1-yl)phenoxy]pyrimidine;

4-(1,3-benzodioxol-5-yl)methylthio-6-chloro-5-methyl-2-[4-(1H-imidazol-1-yl)phenoxy]pyrimidine;

4-[N-(1,3-benzodioxol-5-yl)amino]-6-chloro-5-methyl-2-[4-(1H-imidazol-1-yl)phenoxy]pyrimidine;

4-[N-((1,3-benzodioxol-5-yl)methyl)amino]-6-chloro-5-methyl-2-[4-(1H-imidazol-1-yl)phenoxy]pyrimidine;

4-(1,3-benzodioxol-5-yloxy)-5,6-dimethyl-2-[4-(1H-imidazol-1-yl)phenoxy]pyrimidine;

4-(1,3-benzodioxol-5-yloxy)-6-chloro-5-methyl-2-[4-(1H-imidazol-1-yl)phenoxy]pyrimidine;

2-(1,3-benzodioxol-5-yloxy)-6-chloro-5-methyl-4-[4-(1H-imidazol-1-yl)phenoxy]pyrimidine;
2-(1,3-benzodioxol-5-yl)methoxy-6-chloro-5-methyl-4-[4-(1H-imidazol-1-yl)phenoxy]pyrimidine;
2-(1,3-benzodioxol-5-yl)methylthio-6-chloro-5-methyl-4-[4-(1H-imidazol-1-yl)phenoxy]pyrimidine;
2-(1,3-benzodioxol-5-yl)amino]-6-chloro-5-methyl-4-[4-(1H-imidazol-1-yl)phenoxy]pyrimidine;
2-[((1,3-benzodioxol-5-yl)methyl)amino]-6-chloro-5-methyl-4-[4-(1H-imidazol-1-yl)phenoxy]pyrimidine;
2-(1,3-benzodioxol-5-yloxy)-5,6-dimethyl-4-[4-(1H-imidazol-1-yl)phenoxy]pyrimidine;
2-(1,3-benzodioxol-5-yloxy)-6-chloro-5-methyl-4-[4-(1H-imidazol-1-yl)phenoxy]pyrimidine;
2-[(1,3-benzodioxol-5-yl]methyl]-6-chloro-5-ethyl-4-[4-(1H-imidazol-1-yl)phenoxy]pyrimidine;
2-[(1,3-benzodioxol-5-yl]methyl]-6-chloro-5-(phenyl)methoxy-4-[4-(1H-imidazol-1-yl)phenoxy]pyrimidine;
2-[(1,3-benzodioxol-5-yl]methyl]-6-chloro-5-methoxy-4-[4-(1H-imidazol-1-yl)phenoxy]pyrimidine;
2-[(1,3-benzodioxol-5-yl]methyl]-6-chloro-5-(methoxy)methyl-4-[4-(1H-imidazol-1-yl)phenoxy]pyrimidine;
2-[(1,3-benzodioxol-5-yl]methyl]-6-chloro-5-(methoxycarbonyl)-4-[4-(1H-imidazol-1-yl)phenoxy]pyrimidine;
2-[(1,3-benzodioxol-5-yl]methyl]-6-chloro-5-(methoxycarbonyl)methyl-4-[4-(1H-imidazol-1-yl)phenoxy]pyrimidine;
2-[(1,3-benzodioxol-5-yl]methyl]-5-ethyl-4-[4-(1H-imidazol-1-yl)phenoxy]pyrimidine;
2-[(1,3-benzodioxol-5-yl]methyl]-5-(phenyl)methoxy-4-[4-(1H-imidazol-1-yl)phenoxy]pyrimidine;
2-[(1,3-benzodioxol-5-yl]methyl]-5-methoxy-4-[4-(1H-imidazol-1-yl)phenoxy]pyrimidine;
2-[(1,3-benzodioxol-5-yl]methyl]-5-(methoxy)methyl-4-[4-(1H-imidazol-1-yl)phenoxy]pyrimidine;
2-[(1,3-benzodioxol-5-yl]methyl]-5-(methoxycarbonyl)-4-[4-(1H-imidazol-1-yl)phenoxy]pyrimidine; and
2-[(1,3-benzodioxol-5-yl]methyl]-5-(methoxycarbonyl)methyl-4-[4-(1H-imidazol-1-yl)phenoxy]pyrimidine.

D. Alternatively, compounds of the invention where $R^1$ is nitro are reduced under standard reducing conditions and, if desired, treated with the appropriate alkylating or acylating agent to produce the corresponding amino compounds:
4-(1H-imidazol-1-yl)phenoxy]-2-[(1,3-benzodioxol-5-yl]methyl]-6-chloro-5-aminopyrimidine;
4-(1H-imidazol-1-yl)phenoxy]-2-[(1,3-benzodioxol-5-yl]methyl]-5-(dimethylamino)pyrimidine;
4-(1H-imidazol-1-yl)phenoxy]-2-[(1,3-benzodioxol-5-yl]methyl]-6-chloro-5-(phenylsulfonyl)aminopyrimidine;
4-(1H-imidazol-1-yl)phenoxy]-2-[(1,3-benzodioxol-5-yl]methyl]-5-aminopyrimidine;
4-(1H-imidazol-1-yl)phenoxy]-2-[(1,3-benzodioxol-5-yl]methyl]-5-(dimethylamino)pyrimidine; and
4-(1H-imidazol-1-yl)phenoxy]-2-[(1,3-benzodioxol-5-yl]methyl]-6-chloro-5-(phenylsulfonyl)aminopyrimidine.

EXAMPLE 2

Compounds of the Invention

A. To DMSO (20 mL) was added 2-[(1,3-benzodioxol-5-yl)methyl]-6-chloro-4-[4-(1H-imidazol-1-yl)phenoxy]-5-methylpyrimidine (2 g), and N,N-dimethylpropanediamine (1.5 mL). After heating at 40° C. for 24 hours, the reaction was partitioned with aqueous KOH and $CH_2Cl_2$. The organic layer was separated, washed with water, dried ($MgSO_4$), and the solvent was removed in vacuo. The residue was dissolved in ethanol and HCl (12N, 2 mL) was added. The solvent was removed in vacuo and the residue was crystallized from $CH_2Cl_2$ to give 2.0 g of 2-[(1,3-benzodioxol-5-yl)methyl]-6-[3-(dimethylamino)propyl(methyl)amino]4-[4-(1H-imidazol-1-yl)phenoxy]-5-methylpyrimidine hydrochloride; NMR (DMSO-$d_6$) δ 11.1 (br, 1H), 9.8 (s, 1H), 8.3 (s, 1H), 7.95 (s, 1H), 7.85 (d, 2H), 7.35 (d, 2H), 6.8 (m, 2H), 6.65 (d, 1H), 5.9 (s, 2H), 3.7 (s, 2H), 3.5 (t, 2H), 3.1 (s, 3H), 3.0 (m, 2H), 2.7 (s, 6H), 2.2 (s, 3H), 2.0 (m, 2H) ppm.

B. The following compound was prepared in a similar manner:
2-[(1,3-benzodioxol-5-yl)methyl]-4-[4-(1H-imidazol-1-yl)phenoxy]-6-(morpholin-4-yl)pyrimidine;
NMR (CDCl$_3$) δ 7.85 (s, 1H), 7.4 (d, 2H), 7.2 (m, 4H), 6.85 (s, 1H), 6.75 (m, 2H), 5.9 (s, 2H), 5.75 (s, 1H), 3.8 (s, 2H), 3.75 (m, 4H), 3.6 (m, 4H) ppm.

C. In a similar manner, other compounds of the invention are prepared.

EXAMPLE 3

This example illustrates the preparation of representative pharmaceutical compositions for oral administration containing a compound of the invention, or a pharmaceutically acceptable salt thereof:

| A. | Ingredients | % wt./wt. |
|---|---|---|
| | Compound of the invention | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Compound of the invention | 20.0% |
| | Magnesium stearate | 0.9% |
| | Starch | 8.6% |
| | Lactose | 69.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Compound of the invention | 0.1 g |
| | Propylene glycol | 20.0 g |
| | Polyethylene glycol 400 | 20.0 g |
| | Polysorbate 80 | 1.0 g |
| | Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
|---|---|---|
| | Compound of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Compound of the invention | 1.0% |
| | Methyl or carboxymethyl cellulose | 2.0% |
| | 0.9% saline | q.s. 100 mL |

The compound of the invention is dissolved in the cellulose/saline solution, filtered and bottled for use.

EXAMPLE 4

This example illustrates the preparation of a representative pharmaceutical formulation for parenteral administration containing a compound of the invention, or a pharmaceutically acceptable salt thereof:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 μm membrane filter and packaged under sterile conditions.

EXAMPLE 5

This example illustrates the preparation of a representative pharmaceutical composition in suppository form containing a compound of the invention, or a pharmaceutically acceptable salt thereof:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 6

This example illustrates the preparation of a representative pharmaceutical formulation for insufflation containing a compound of the invention, or a pharmaceutically acceptable salt thereof:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 7

This example illustrates the preparation of a representative pharmaceutical formulation in nebulized form containing a compound of the invention, or a pharmaceutically acceptable salt thereof:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 8

This example illustrates the preparation of a representative pharmaceutical formulation in aerosol form containing a compound of the invention, or a pharmaceutically acceptable salt thereof:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 9

In Vitro Assay

RAW 264.7 murine macrophage cells were obtained from American Type Culture Collection (Rockville, Md.) and were maintained in RPMI 1640 containing 10% fetal bovine serum (FBS), 5000 units/mL of penicillin and streptomycin, and 2 mM glutamine (maintenance medium). Nitric oxide synthase activity was measured by a fluorescent assay of the NO oxidation product, nitrite (Diamani et al., *Talanta* (1986), Vol. 33,pp. 649–652). Induction o iNOS is stimulated by treatment of the cells with lipopolysaccharide and γ-interferon. The assay is described in more detail below.

The cells were harvested, diluted to 500,000 cells/mL with maintenance medium, and seeded into 96-well plates at 100 μL/well. The plates were incubated overnight at 37° C., under a 5% $CO_2$ atmosphere. The medium was then replaced with 90 μL of BME medium containing 10% FBS, 100 units/mL of penicillin, 100 μL streptomycin, 2 mM glutamine, 100 units/mL of γ-interferon and 2 μg/mL of lipopolysaccharide. N-guanidino-methyl-L-arginine was added to four wells (negative control) at a final concentration of 200 µM using 10 µL of 2 mM stock solution in 100 mM Hepes, pH 7.3+0.1% DMSO and four wells received only the 100 mM Hepes/0.1% DMSO buffer (positive control). Compounds of the invention were dissolved at 10-fold the desired final concentration in Hepes/DMSO and 10 µL of these solutions was transferred to the 96-well plate. The plates were incubated for 17 hrs at 37° C., under a 5% $CO_2$ atmosphere. Nitrite accumulation in the culture medium was determined as follows: To each well was added 15 µL of 2,3-diaminonaphthalene (10 µg/mL in 0.75 M HCl) and each well was then incubated for 10 minutes at room temperature. To each well was then added 15 µL of 1 N NaOH and the fluorescence emission was measured at 405 nm, using an excitation wavelength of 365 nm. Enzyme activity in the experimental wells was normalized to percent control using the positive and negative control values. The signal to noise ratio was >10 for the assay.

The compounds of the invention, when tested in this assay, demonstrated the ability to inhibit NO production in vitro.

EXAMPLE 10

In Vitro Assay

A. A172 cells were obtained from the American Type Culture Collection, and were cultured routinely in DMEM without phenol red or sodium pyruvate but containing high glucose (Gibco BRL), supplemented with 10% (v/v) fetal bovine serum (Gibco BRL), in a humidified atmosphere of 5% $CO_2$ in air at 37° C. Cells were harvested and plated at 100,000 cells/well into 96-well tissue culture dishes in a total of 100 µL of culture medium. 18–24 hours later, iNOS activity was induced by the addition of 222 U/ml human γ-interferon, 22 ng/ml of human tumor necrosis factor α, and 2.2 ng/mL of human interleukin-1β. All cytokines were purchased from Boehringer Mannheim. Concomitant with cytokine addition, the appropriate concentration of the compound of the invention was also added. Compound stock solutions were prepared in DMSO, and vehicle was added to control wells. Final concentration of DMSO in the incubations was less than 0.2%, and had no influence on iNOS induction or activity measurements. Incubations were continued for 18–24 hours, at which time an aliquot of the culture medium was removed and tested for nitrite concentration using the Griess reagent (see below).

B. Following incubation with cytokines plus compound, a 100 µL aliquot of the culture medium was removed and mixed with 150 µL of the Griess reagent (5% v/v phosphoric acid containing 2% w/v sulfanilamide plus 0.2% w/v naphthylethylenediamine) in a separate 96-well plate. The plates were read within 15 min at 550 nm in a SpectraMax spectrophotometer. The inhibition of iNOS activity by compound resulted in a decrease in the OD550 of the medium. $IC_{50}$ values were calculated from a log-logit analysis of the data. Inhibition curves with Hill slopes of less than 0.5 or greater than 1.5 were rejected.

Control experiments showed that no significant conversion of nitrite to nitrate occurred over the course of an experiment. Cells incubated in the absence of cytokines produced no measurable nitrite. Therefore, measuring the nitrite content of the culture medium of cytokine-induced cells is a simple, accurate means of measuring the induction of iNOS activity in these cells.

Compounds of the invention, when tested in this assay, demonstrated the ability to inhibit nitric oxide production in vitro.

EXAMPLE 11

In Vivo Assay

Effects of Compounds of the Invention on Adjuvant-Induced Arthritis in Rats

Male Lewis rats are injected intradermally (proximal quarter of the tail) with 0.1 mL of *Mycobacterium butyricum* in Incomplete Freund's Adjuvant (10 mg/mL). Either the vehicle (acidified saline, 1 mL/kg) or a compound of the invention (3, 10, or 30 mg/kg) is administered subcutaneously (b.i.d.), starting on the day following adjuvant immunization, and continued until the end of the experiment (N=10 rats per treatment group). Clinical scores (see below) are measured in all limbs 3 times per week throughout the study. Rats are euthanized 34–35 days after immunization. At the time of euthanasia, a radiologic evaluation (see below) of the hind paws is performed, a blood sample is collected for clinical blood chemistry and drug levels (high dose group only; 6 or 12 hours post final dose), a section of liver is obtained for measurement of potential toxicity, and the hind limbs are preserved for histopathological determination.

Clinical scoring-each limb is graded according to the following scale:

0  no signs of inflammation
1  moderate redness, first indication of swelling, joint flexible
2  moderate redness, moderate swelling, joint flexible
3  redness, significant swelling and distortion of the paw, joint beginning to fuse
4  redness, gross swelling and distortion of the paw, joint completely fused Radiological scoring—each hind limb is graded on a scale of 0–3 for each of the following parameters:

soft tissue swelling cartilage loss erosion heterotropic ossification

The compounds of the invention, when tested in this assay, demonstrate the ability to treat the arthritis present in the rats.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound selected from the group consisting of the following formulae:

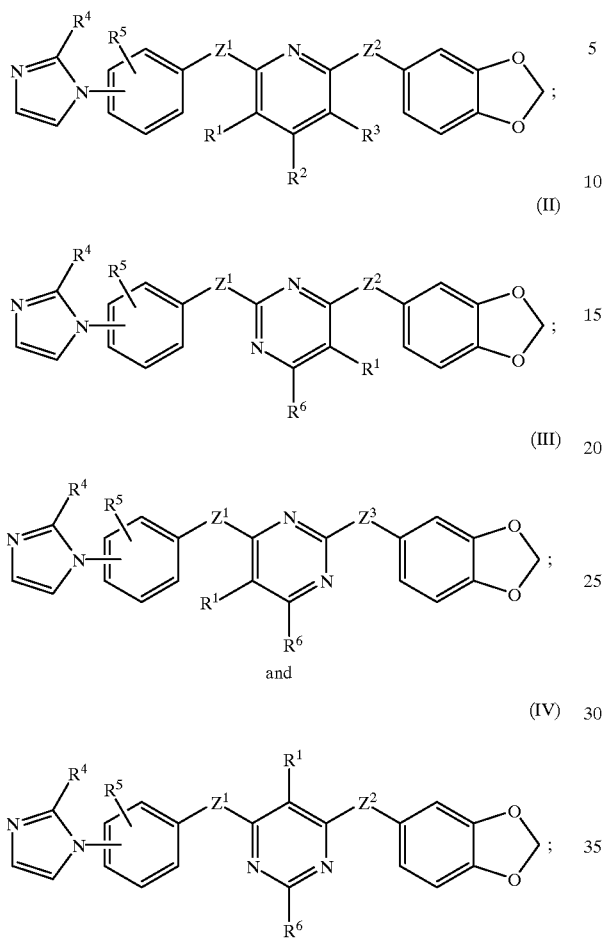

wherein:
  each $Z^1$ is independently —$(CH_2)_m$—O— (where m is 0 to 2), —$(CH_2)_m$—S— (where m is 0 to 2), or —$(CH_2)_m$—N($R^7$)— (where m is 0 to 2);
  each $Z^2$ is independently —O—$(CH_2)_m$— (where m is 0 to 2), —S—$(CH_2)_m$— (where m is 0 to 2), or —N($R^7$)—$(CH_2)_m$— (where m is 0 to 2);
  $Z^3$ is —$(CH_2)_n$— (where n is 1 to 4), —O—$(CH_2)_m$— (where m is 0 to 2), —S—$(CH_2)_m$— (where m is 0 to 2), or —N($R^7$)—$(CH_2)_m$— (where m is 0 to 2);
  each $R^1$ and $R^3$ are independently selected from the group consisting of hydrogen, halo, alkyl, haloalkyl, nitro, aralkoxy, —$OR^8$, —$R^{11}$—$OR^8$, —N($R^8$)$R^9$, —C(O)$OR^8$, —$R^{11}$—C(O)$OR^8$, —C(O)N($R^8$)$R^9$, —$R^{11}$—C(O)N($R^8$)$R^9$, —C(O)N($R^8$)$CH_2$C(O)N($R^8$)$R^9$, —N($R^8$)C(O)N($R^8$)$R^9$, —N($R^8$)C(O)$R^9$, —N($R^8$)S(O)$_2R^{10}$, and —N($R^8$)C(O)N($R^8$)—$CH_2$C(O)N($R^8$)$R^9$;
  $R^2$ is hydrogen, alkyl, bromo, iodo, —N($R^7$)—$(CH_2)_p$—N($R^8$)$R^9$ (where p is 1 to 4), —$(CH_2)_q$—N($R^7$)—$CH_2$—C(O)—$OR^8$ (where q is 0 to 3), 4-morpholinyl, 1-piperidinyl, 1-piperazinyl, or 1-pyrrolidinyl;
  each $R^4$ is independently hydrogen or alkyl;
  each $R^5$ is independently hydrogen, halo, haloalkyl, alkyl, nitro, —$OR^8$, —C(O)$OR^8$, —C(O)N($R^8$)$R^9$, —N($R^8$)$R^9$, —N($R^8$)C(O)$R^8$, or —N(H)S(O)$_2R^{10}$;

each $R^6$ is independently hydrogen, alkyl, aryl, aralkyl, halo, —N($R^8$)$R^9$, —N($R^7$)—$(CH_2)_p$—N($R^8$)$R^9$ (where p is 1 to 4), —$(CH_2)_q$—N($R^7$)—$CH_2$—C(O)$OR^8$ (where q is 0 to 3), 4-morpholinyl, 1-piperidinyl, 1-piperazinyl, or 1-pyrrolidinyl;
  each $R^7$ is hydrogen or alkyl;
  each $R^8$ and $R^9$ is independently hydrogen, alkyl, aryl (optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), or aralkyl (wherein the aryl is optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl);
  each $R^{10}$ is alkyl, aryl (optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), or aralkyl (wherein the aryl is optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), and
  each $R^{11}$ is independently an alkylene or alkylidene chain;
  as a single stereoisomer or a mixture thereof; or a pharmaceutically acceptable salt thereof.

2. The compound of claim 1 selected from formula (I):

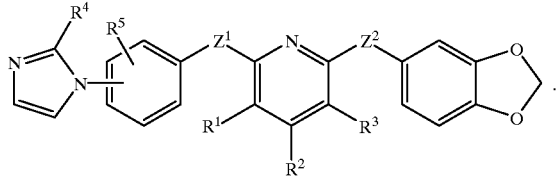

3. The compound of claim 2 wherein:
  $Z^1$ is —O— or —$(CH_2)_m$—N($R^7$)— (where m is 0 to 2);
  $Z^2$ is —O—$(CH_2)_m$— (where m is 0 to 2), —S—$(CH_2)_m$— (where m is 0 to 2), or —N($R^7$)—$(CH_2)_m$— (where m is 0 to 2);
  $R^1$ and $R^3$ are independently selected from the group consisting of hydrogen, halo, and alkyl;
  $R^2$ is hydrogen, alkyl, bromo, iodo, —N($R^7$)—$(CH_2)_p$—N($R^8$)$R^9$ (where p is 1 to 4), —$(CH_2)_q$—N($R^7$)—$CH_2$—C(O)—$OR^8$ (where q is 0 to 3), 4-morpholinyl, 1-piperidinyl, 1-piperazinyl, or 1-pyrrolidinyl;
  $R^4$ is hydrogen or alkyl;
  $R^5$ is hydrogen, halo, haloalkyl, alkyl, nitro, —$OR^8$, —C(O)$OR^8$, —C(O)N($R^8$)$R^9$, —N($R^8$)$R^9$, —N($R^8$)C(O)$R^8$, or —N(H)S(O)$_2R^{10}$;
  each $R^7$ is hydrogen or alkyl; and
  each $R^8$ and $R^9$ is independently hydrogen or alkyl.

4. The compound of claim 3 wherein:

$Z^1$ is —O—;

$Z^2$ is —O—$(CH_2)_m$— (where m is 0 to 2), —S—$(CH_2)_m$— (where m is 0 to 2), or —N($R^7$)—$(CH_2)_m$— (where m is 0 to 2);

$R^1$ and $R^3$ are independently selected from the group consisting of hydrogen, chloro, and fluoro;

$R^2$ is hydrogen, alkyl, bromo, iodo, —N($R^7$)—$(CH_2)_p$—N($R^8$)$R^9$ (where p is 1 to 4), —$(CH_2)_q$—N($R^7$)—$CH_2$—C(O)—OR (where q is 0 to 3), 4-morpholinyl, 1-piperidinyl, 1-piperazinyl, or 1-pyrrolidinyl;

$R^4$ and $R^5$ are each independently hydrogen or alkyl; and each $R^7$, $R^8$ and $R^9$ is each independently hydrogen or alkyl.

5. The compound of claim 4 wherein:

$Z^1$ and $Z^2$ are both —O—;

$R^1$ and $R^3$ are independently selected from the group consisting of hydrogen, chloro, and fluoro;

$R^2$ is hydrogen, alkyl or —N($R^7$)—$CH_2$—C(O)—$OR^8$;

$R^4$ and $R^5$ are each independently hydrogen or alkyl; and each $R^7$ and $R^8$ is each independently hydrogen or alkyl.

6. The compound of claim 5 wherein:

$R^1$, $R^2$, and $R^3$ are each hydrogen;

$R^4$ is hydrogen; and $R^5$ is hydrogen or methyl.

7. The compound of claim 6 selected from the group consisting of the following compounds:

2-(1,3-benzodioxol-5-yloxy)-6-[4-(1H-imidazol-1-yl)phenoxy]pyridine; and 2-(1,3-benzodioxol-5-yloxy)-6-[4-(1H-imidazol-1-yl)-2-methylphenoxy]pyridine.

8. The compound of claim 5 wherein:

$R^1$ and $R^3$ are independently fluoro or chloro;

$R^2$ is hydrogen, alkyl or —N($R^7$)—$CH_2$—C(O)—$OR^8$;

$R^4$ is hydrogen;

$R^5$ is hydrogen or alkyl;

$R^7$ is methyl; and $R^8$ is hydrogen, methyl or ethyl.

9. The compound of claim 8 selected from the group consisting of the following compounds:

2-(1,3-benzodioxol-5-yloxy)-3,5-difluoro-6-[4-(1H-imidazol-1-yl)phenoxy]-4-methylpyridine;

2-(1,3-benzodioxol-5-yloxy)-3,5-difluoro-6-[3-(1H-imidazol-1-yl)phenoxy]-4-methylpyridine; and 2-(1,3-benzodioxol-5-yloxy)-3,5-difluoro-6-[4-(1H-imidazol-1-yl)phenoxy]-4-[(N-methyl-N-((ethoxycarbonyl)methyl)amino]pyridine.

10. The compound of claim 4 wherein:

$Z^1$ is —O—;

$Z^2$ is —N($R^7$)—$(CH_2)_m$— (where m is 0 to 2);

$R^1$ and $R^3$ are independently selected from the group consisting of hydrogen, chloro, and fluoro;

$R^2$ is hydrogen, alkyl or —N($R^7$)—$CH_2$—C(O)—$OR^8$; and $R^4$, $R^5$, $R^7$, and $R^8$ are each independently hydrogen or alkyl.

11. The compound of claim 10 wherein $Z^1$ is —O—;

$Z^2$ is —N($R^7$)—$CH_2$—;

$R^1$ and $R^3$ are independently selected from the group consisting of hydrogen, chloro, and fluoro;

$R^2$ is hydrogen or methyl;

$R^4$ and $R^5$ are each independently hydrogen or alkyl; and $R^7$ is hydrogen or alkyl.

12. The compound of claim 11, namely, 2-(4-(1H-imidazol-1-yl)phenoxy)-3,5-difluoro-4-methyl-6-[((1,3-benzodioxol-5-yl)methyl)amino]pyridine.

13. The compound of claim 1 selected from formula (II):

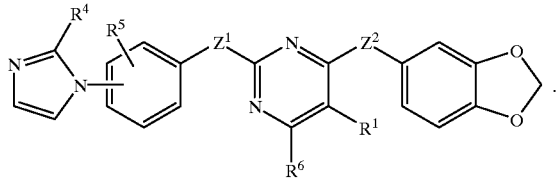

(II)

14. The compound of claim 13 wherein:

$Z^1$ is —O— or —$(CH_2)_m$—N($R^7$)— (where m is 0 to 2);

$Z^2$ is —O—$(CH_2)_m$— (where m is 0 to 2), —S—$(CH_2)_m$— (where m is 0 to 2), or —N($R^7$)—$(CH_2)_m$— (where m is 0 to 2);

$R^1$ is hydrogen, halo, or alkyl;

$R^4$ is hydrogen or alkyl;

$R^5$ is hydrogen, halo, haloalkyl, alkyl, nitro, —$OR^8$, —C(O)$OR^8$, —C(O)N($R^8$)$R^9$, —N($R^8$)$R^9$, —N($R^8$)C(O)$R^8$, or —N(H)S(O)$_2R^{10}$;

$R^6$ is hydrogen, alkyl, aryl, aralkyl, halo, —N($R^8$)$R^9$, —N($R^7$)—$(CH_2)_p$—N($R^8$)$R^9$ (where p is 1 to 4), —$(CH_2)_q$—N($R^7$)—$CH_2$—C(O)$OR^8$ (where q is 0 to 3), 4-morpholinyl, 1-piperidinyl, 1-piperazinyl, or 1-pyrrolidinyl;

each $R^7$ is independently hydrogen or alkyl; and each $R^8$ and $R^9$ is independently hydrogen or alkyl.

15. The compound of claim 14 wherein:

$Z^1$ and $Z^2$ are both —O—;

$R^1$ is hydrogen, chloro, or fluoro;

$R^4$ is hydrogen or alkyl;

$R^5$ is hydrogen, halo, haloalkyl or alkyl;

$R^6$ is hydrogen, alkyl or —$(CH_2)_q$—N($R^7$)—$CH_2$—C(O)—$OR^8$ (where q is 0 or 1);

$R^7$ is hydrogen or alkyl; and $R^8$ is hydrogen or alkyl.

16. The compound of claim 15 wherein:

$R^4$ is hydrogen;

$R^5$ is hydrogen, chloro, fluoro, trifluoromethyl or alkyl;

$R^6$ is hydrogen, methyl, or —$CH_2$—N($R^7$)—$CH_2$—C(O)—$OR^8$;

$R^7$ is hydrogen or methyl; and $R^8$ is hydrogen or alkyl.

17. The compound of claim 16 selected from the group consisting of the following compounds:

4-(1,3-benzodioxol-5-yloxy)-2-[4-(1H-imidazol-1-yl)phenoxy]pyrimidine;

4-(1,3-benzodioxol-5-yloxy)-2-[4-(1H-imidazol-1-yl)phenoxy]-6-methylpyrimidine;

4-(1,3-benzodioxol-5-yloxy)-2-[2-fluoro-4-(1H-imidazol-1-yl)phenoxy]-6-methylpyrimidine;

4-(1,3-benzodioxol-5-yloxy)-2-[3-chloro-4-(1H-imidazol-1-yl)phenoxy]-6-methylpyrimidine; and 4-(1,3-benzodioxol-5-yloxy)-2-[3-trifluoromethyl-4-(1H-imidazol-1-yl)phenoxy]-6-methylpyrimidine.

18. The compound of claim 1 selected from formula (III):

(III)

19. The compound of claim 18 wherein:
$Z^1$ is —O— or —(CH$_2$)$_m$—N(R$^7$)— (where m is 0 to 2);
$Z^3$ is —O—, —(CH$_2$)$_n$— (where n is 1 to 4), or —N(R$^7$)—(CH$_2$)$_m$— (where m is 0 to 2);
$R^1$ is hydrogen, halo, or alkyl;
$R^4$ is hydrogen or alkyl;
$R^5$ is hydrogen, halo, haloalkyl, alkyl, nitro, —OR$^8$, —C(O)OR$^8$, —C(O)N(R$^8$)R$^9$, —N(R$^8$)R$^9$, —N(R$^8$)C(O)R$^8$, or —N(H)S(O)$_2$R$^{10}$;
$R^6$ is hydrogen, alkyl, aryl, aralkyl, halo, —N(R$^8$)R$^9$, —N(R$^7$)—(CH$_2$)$_p$—N(R$^8$)R$^9$ (where p is 1 to 4), —(CH$_2$)$_q$—N(R$^7$)—CH$_2$—C(O)OR$^8$ (where q is 0 to 3), 4-morpholinyl, 1-piperidinyl, 1-piperazinyl, or 1-pyrrolidinyl;
each $R^7$ is hydrogen or alkyl; and
each $R^8$ and $R^9$ is independently hydrogen or alkyl.

20. The compound of claim 19 wherein:
$Z^1$ is —O—;
$Z^3$ is —O— or —CH$_2$—;
$R^1$ is hydrogen, chloro, fluoro or methyl;
$R^4$ and $R^5$ are independently hydrogen or alkyl;
$R^6$ is hydrogen, alkyl, aryl, aralkyl, halo, —N(R$^8$)R$^9$, —N(R$^7$)—(CH$_2$)$_p$—N(R$^8$)R$^9$ (where p is 1 to 4), —(CH$_2$)$_q$—N(R$^7$)—CH$_2$—C(O)OR$^8$ (where q is 0 to 3), 4-morpholinyl, 1-piperidinyl, 1-piperazinyl, or 1-pyrrolidinyl; and
each $R^7$, $R^8$, and $R^9$ is hydrogen or alkyl.

21. The compound of claim 20 wherein:
$R^1$ is hydrogen or methyl; and
$R^6$ is hydrogen, methyl, chloro, fluoro, 4-morpholinyl or —N(R$^7$)—(CH$_2$)$_m$—N(R$^8$)R$^9$ (where m is 1 to 4).

22. The compound of claim 21 wherein:
$R^4$ is hydrogen;
$R^5$ is hydrogen;
$R^7$ is hydrogen or methyl; and
$R^8$ and $R^9$ are independently hydrogen or methyl.

23. The compound of claim 22 selected from the group consisting of the following compounds:
2-(1,3-benzodioxol-5-yloxy)-4-[4-(1H-imidazol-1-yl)phenoxy]pyrimidine;
2-(1,3-benzodioxol-5-yloxy)-4-[4-(1H-imidazol-1-yl)phenoxy]-5-methylpyrimidine;
2-[(1,3-benzodioxol-5-yl)methyl]-6-chloro-4-[4-(1H-imidazol-1-yl)phenoxy]pyrimidine;
2-[(1,3-benzodioxol-5-yl)methyl]-6-[3-(dimethylamino)propyl(methyl)amino]-4-[4-(1H-imidazol-1-yl)phenoxy]-5-methylpyrimidine; and
2-[(1,3-benzodioxol-5-yl)methyl]-4-[4-(1H-imidazol-1-yl)phenoxy]-6-(morpholin-4-yl)pyrimidine.

24. The compound of claim 1 selected from formula (IV):

(IV)

25. The compound of claim 24 wherein:
$Z^1$ is —O— or —(CH$_2$)$_m$—N(R$^7$)— (where m is 0 to 2);
$Z^2$ is —O—(CH$_2$)$_m$— (where m is 0 to 2), —S—(CH$_2$)$_m$— (where m is 0 to 2), or —N(R$^7$)—(CH$_2$)$_m$— (where m is 0 to 2);
$R^1$ is hydrogen, halo, or alkyl;
$R^4$ is hydrogen or alkyl;
$R^5$ is hydrogen, halo, haloalkyl, alkyl, nitro, —OR$^8$, —C(O)OR$^8$, —C(O)N(R$^8$)R$^9$, —N(R$^8$)R$^9$, —N(R$^8$)C(O)R$^8$, or —N(H)S(O)$_2$R$^{10}$;
$R^6$ is hydrogen or alkyl;
each $R^7$ is hydrogen or alkyl; and
each $R^8$ and $R^9$ is independently hydrogen or alkyl.

26. The compound of claim 25 wherein:
$Z^1$ and $Z^2$ are both —O—;
$R^1$ is hydrogen, chloro, or fluoro; and
$R^4$, $R^5$ and $R^6$ are independently hydrogen or alkyl.

27. The compound of claim 26, namely, 6-(1,3-benzodioxol-5-yloxy)-4-[4-(1H-imidazol-1-yl)phenoxy]pyrimidine.

28. A pharmaceutical composition comprising a pharmaceutically acceptable excipient and a compound selected from the group consisting of the following formulae:

(I)

(II)

(III)

-continued and

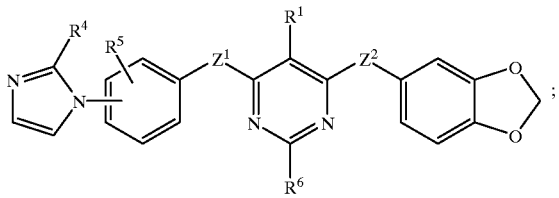
(IV)

wherein:

each $Z^1$ is independently —$(CH_2)_m$—O— (where m is 0 to 2), —$(CH_2)_m$—S— (where m is 0 to 2), or —$(CH_2)_m$—N($R^7$)— (where m is 0 to 2);

each $Z^2$ is independently —O—$(CH_2)_m$— (where m is 0 to 2), —S—$(CH_2)_m$— (where m is 0 to 2), or —N($R^7$)—$(CH_2)_m$— (where m is 0 to 2);

$Z^3$ is —$(CH_2)_n$— (where n is 1 to 4), —O—$(CH_2)_m$— (where m is 0 to 2), —S—$(CH_2)_m$— (where m is 0 to 2), or —N($R^7$)—$(CH_2)_m$— (where m is 0 to 2);

each $R^1$ and $R^3$ are independently selected from the group consisting of hydrogen, halo, alkyl, haloalkyl, nitro, aralkoxy, —$OR^8$, —$R^{11}$—$OR^8$, —N($R^8$)$R^9$, —C(O)$OR^8$, —$R^{11}$—C(O)$OR^8$, —C(O)N($R^8$)$R^9$, —$R^{11}$—C(O)N($R^8$)$R^9$, —C(O)N($R^8$)$CH_2$C(O)N($R^8$)$R^9$, —N($R^8$)C(O)N($R^8$)$R^9$, —N($R^8$)C(O)$R^9$, —N($R^8$)S(O)$_2R^{10}$, and —N($R^8$)C(O)N($R^8$)—$CH_2$C(O)N($R^8$)$R^9$;

$R^2$ is hydrogen, alkyl, bromo, iodo, —N($R^7$)—$(CH_2)_p$—N($R^8$)$R^9$ (where p is 1 to 4), —$(CH_2)_q$—N($R^7$)—$CH_2$—C(O)—$OR^8$ (where q is 0 to 3), 4-morpholinyl, 1-piperidinyl, 1-piperazinyl, or 1-pyrrolidinyl;

each $R^4$ is independently hydrogen or alkyl;

each $R^5$ is independently hydrogen, halo, haloalkyl, alkyl, nitro, —$OR^8$, —C(O)$OR^8$, —C(O)N($R^8$)$R^9$, —N($R^8$)$R^9$, —N($R^8$)C(O)$R^8$, or —N(H)S(O)$_2R^{10}$;

each $R^8$ is independently hydrogen, alkyl, aryl, aralkyl, halo, —N($R^8$)$R^9$, —N($R^7$)—$(CH_2)_p$—N($R^8$)$R^9$ (where p is 1 to 4), —$(CH_2)_q$—N($R^7$)—$CH_2$—C(O)$OR^8$ (where q is 0 to 3), 4-morpholinyl, 1-piperidinyl, 1-piperazinyl, or 1-pyrrolidinyl;

each $R^7$ is hydrogen or alkyl;

each $R^8$ and $R^9$ is independently hydrogen, alkyl, aryl (optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), or aralkyl (wherein the aryl is optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl);

each $R^{10}$ is alkyl, aryl (optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), or aralkyl (wherein the aryl is optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), and each $R^{11}$ is independently an alkylene or alkylidene chain;

as a single stereoisomer or a mixture thereof; or a pharmaceutically acceptable salt thereof.

29. A method of treating a disease in a mammal which comprises administering to said mammal having said disease a therapeutically effective amount of a compound selected from the group consisting of the following formulae:

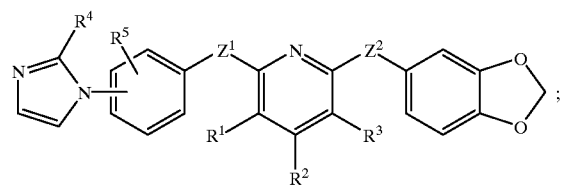
(I)

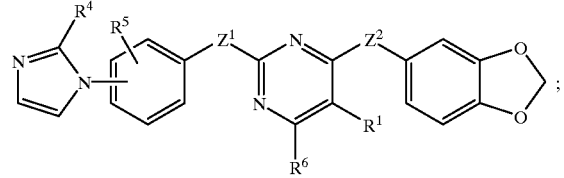
(II)

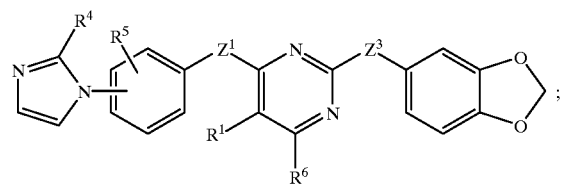
(III)

and

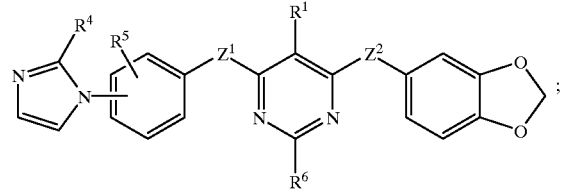
(IV)

wherein:

each $Z^1$ is independently —$(CH_2)_m$—O— (where m is 0 to 2), —$(CH_2)_m$—S— (where m is 0 to 2), or —$(CH_2)_m$—N($R^7$)— (where m is 0 to 2);

each $Z^2$ is independently —O—$(CH_2)_m$— (where m is 0 to 2), —S—$(CH_2)_m$— (where m is 0 to 2), or —N($R^7$)—$(CH_2)_m$— (where m is 0 to 2);

$Z^3$ is —$(CH_2)_n$— (where n is 1 to 4), —O—$(CH_2)_m$— (where m is 0 to 2), —S—$(CH_2)_m$— (where m is 0 to 2), or —N($R^7$)—$(CH_2)_m$— (where m is 0 to 2);

each $R^1$ and $R^3$ are independently selected from the group consisting of hydrogen, halo, alkyl, haloalkyl, nitro, aralkoxy, —OR$^8$, —R$^{11}$—OR$^8$, —N(R$^8$)R$^9$, —C(O)OR$^8$, —R$^{11}$—C(O)OR$^8$, —C(O)N(R$^8$)R$^9$, —R$^{11}$—C(O)N(R$^8$)R$^9$, —C(O)N(R$^8$)CH$_2$C(O)N(R$^8$)R$^9$, —N(R$^8$)C(O)N(R$^8$)R$^9$, —N(R$^8$)C(O)R$^9$, —N(R$^8$)S(O)$_2$R$^{10}$, and —N(R$^8$)C(O)N(R$^8$)—CH$_2$C(O)N(R$^8$)R$^9$;

R$^2$ is hydrogen, alkyl, bromo, iodo, —N(R$^7$)—(CH$_2$)$_p$—N(R$^8$)R$^9$ (where p is 1 to 4), —(CH$_2$)$_q$—N(R$^7$)—CH$_2$—C(O)—OR$^8$ (where q is 0 to 3), 4-morpholinyl, 1-piperidinyl, 1-piperazinyl, or 1-pyrrolidinyl;

each R$^4$ is independently hydrogen or alkyl;

each R$^5$ is independently hydrogen, halo, haloalkyl, alkyl, nitro, —OR$^8$, —C(O)OR$^8$, —C(O)N(R$^8$)R$^9$, —N(R$^8$)R$^9$, —N(R$^8$)C(O)R$^8$, or —N(H)S(O)$_2$R$^{10}$;

each R$^6$ is independently hydrogen, alkyl, aryl, aralkyl, halo, —N(R$^8$)R$^9$, —N(R$^7$)—(CH$_2$)$_p$—N(R$^8$)R$^9$ (where p is 1 to 4), —(CH$_2$)$_q$—N(R$^7$)—CH$_2$—C(O)OR$^8$ (where q is 0 to 3), 4-morpholinyl, 1-piperidinyl, 1-piperazinyl, or 1-pyrrolidinyl;

each R$^7$ is hydrogen or alkyl;

each R$^8$ and R$^9$ is independently hydrogen, alkyl, aryl (optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), or aralkyl (wherein the aryl is optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl);

each R$^{10}$ is alkyl, aryl (optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), or aralkyl (wherein the aryl is optionally substituted by one or more substituents selected from the group consisting of halo, alkyl, aryl, aralkyl, hydroxy, alkoxy, aralkoxy, amino, dialkylamino, monoalkylamino, nitro, carboxy, alkoxycarbonyl, aminocarbonyl, monoalkylaminocarbonyl, and dialkylaminocarbonyl), and each R$^{11}$ is independently an alkylene or alkylidene chain;

as a single stereoisomer or a mixture thereof; or a pharmaceutically acceptable salt thereof, wherein the disease is characterized by production of nitric oxide by the inducible form of nitric oxide synthase and wherein the selected compound inhibits said production of nitric oxide.

30. The method according to claim 29 wherein said disease is selected from the group consisting of multiple sclerosis, stroke or cerebral ischemia, Alzheimer's disease, HIV dementia, Parkinson's disease, meningitis, dilated cardiomyopathy and congestive heart failure, atherosclerosis, restenosis or graft stenosis, septic shock, hemorrhagic shock, asthma, adult respiratory distress syndrome, smoke or particulate-mediated lung injury, pathogen-mediated pneumonias, rheumatoid arthritis and osteoarthritis, glomerulonephritis, systemic lupus erythematosus, inflammatory bowel diseases, insulin dependent diabetes mellitus, diabetic neuropathy or nephropathy, acute and chronic organ transplant rejection, transplant vasculopathies, graft-versus-host disease, psoriasis, and cancer.

31. The method of claim 30 wherein said disease is multiple sclerosis.

32. The method of claim 30 wherein said disease is rheumatoid arthritis.

33. The method of claim 30 wherein said disease is dilated cardiomyopathy.

34. The method of claim 30 wherein said disease is congestive heart failure.

35. The method of claim 30 wherein the disease is stroke or cerebral isohemia.

36. The method of claim 30 wherein the disease is septic shock.

\* \* \* \* \*